(12) United States Patent
Radisic et al.

(10) Patent No.: US 8,367,410 B2
(45) Date of Patent: Feb. 5, 2013

(54) APPLICATION OF ELECTRICAL STIMULATION FOR FUNCTIONAL TISSUE ENGINEERING IN VITRO AND IN VIVO

(75) Inventors: Milica Radisic, Cambridge, MA (US);
Hyoungshin Park, Somerville, MA (US); Robert Langer, Newton, MA (US); Lisa Freed, Lexington, MA (US); Gordana Vunjak-Novakovic, Belmont, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 327 days.

(21) Appl. No.: 10/872,577

(22) Filed: Jun. 21, 2004

(65) Prior Publication Data
US 2005/0112759 A1 May 26, 2005

Related U.S. Application Data

(60) Provisional application No. 60/480,214, filed on Jun. 20, 2003.

(51) Int. Cl.
*C12N 5/00* (2006.01)
*C12N 5/02* (2006.01)
*C12N 5/07* (2010.01)

(52) U.S. Cl. ..... 435/395; 435/375; 435/377; 435/173.1; 623/23.72

(58) Field of Classification Search .................. 435/366, 435/375, 395, 377; 424/423; 623/14.13, 623/23.72, 23.75
See application file for complete search history.

(56) References Cited

U.S. PATENT DOCUMENTS

| | | | |
|---|---|---|---|
| 4,721,096 A | 1/1988 | Naughton et al. | |
| 4,963,489 A | 10/1990 | Naughton et al. | |
| 5,429,938 A * | 7/1995 | Humes | 435/377 |
| 5,820,918 A * | 10/1998 | Ronan et al. | 427/2.1 |
| 5,843,766 A * | 12/1998 | Applegate et al. | 435/284.1 |
| 6,190,893 B1 * | 2/2001 | Shastri et al. | 435/173.8 |
| 6,287,340 B1 * | 9/2001 | Altman et al. | 623/13.11 |
| 6,291,240 B1 * | 9/2001 | Mansbridge et al. | 435/395 |
| 6,387,369 B1 | 5/2002 | Pittenger et al. | |
| 6,454,787 B1 * | 9/2002 | Maddalo et al. | 606/214 |
| 2002/0115208 A1 * | 8/2002 | Mitchell et al. | 435/325 |
| 2008/0318315 A1 * | 12/2008 | Martin et al. | 435/377 |

OTHER PUBLICATIONS

Colter, DC et al. Identification of a subpopulation of rapidly self-renewing and multipotential adult stem cells in colonies of human marrow stromal cells. PNAS. 2001. 98(14): 7841-7845.*
Akins et al., Tissue Eng. 1999, 5: 103-118.
Ameer et al., J. Orthop. Res. 2002, 20: 16-19.
Asahara et al., Science, 1997, 275: 964-967.
Ashton et al., Clin. Orthop. 1980, 151: 294-307.
Bittner et al., Anat. Embryol. 1999, 199: 391-396.
Brazelton et al., Science, 2000, 290: 1775-1779.
Bursac et al., Am. J. Physiol. Heart Circ. Physiol. 1999, 277: H433-H444.
Carrier et al. Biotechnol. Bioeng. 1999, 64: 580-589.
Carrier et al. Biotechnol. Bioeng. 2002, 78: 617-625.
Carrier et al. Tissue Eng. 2002, 8: 175-188.
Casey, et al., Circulation, 102: 3124-3129, 2000.
Claycomb et al., Proc. Natl. Acad. Sci. USA, 1998, 95: 2979-2984.
Eglitis and E. Mezey, Proc. Natl. Acad. Sci. USA, 1997, 94: 4080-4085.
Eschenhagen et al., FASEB J. 1997, 11: 683-694.
Eschenhagen et al., Transplant Immunol. 2002, 9: 315-321.
Ferrari et al., Science, 1998, 279: 1528-1530.
Fink et al., FASEB J. 2000, 14: 669-679.
Freed and G. Vunjak-Novakovic, in Vitro Cell Dev. Biol. 1997, 33: 381-385.
Freerksen et al., J. Cell. Physiol., 1984, 120: 126-134.
Friedenstein et al., Cell Tissue Kinet. 1987, 20: 263-272.
Gussoni et al., Nature, 1999, 401: 390-394.
Hoyt et al., Circ. Res. 1989, 64: 563-574.
Huguet et al., J. Biol. Chem. 1995, 270: 12851-12856.
Itskowitz-Eldor et al., Mol. Med. 2000, 6: 88-95.
Jackson et al., J. Clin. Invest. 2001, 107: 1395-1402.
Karliner et al., Biochem. Biophys. Res. Comm. 1985. 128: 376-382.
Kessler-Icekson et al., Exp. Cell Res. 1984. 155: 113-120.
Kim et al., Tissue Eng. 2000, 6: 39-44.
Kitamura et al., Am. J. Physiol. 1996, 270(4 Pt 2): F614-F622.
Kopen et al., Proc. Natl. Acad. Sci. USA, 1999, 96: 10711-10716.
Krause et al., Cell, 2001, 105: 369-377.
Lagasse et al., Nat. Med. 2000, 6: 1229-1234.
Leor et al., Circulation, 2000, 102:II56-II61.
Li et al., Circulation, 1999, 100: II63-II69.
Li et al., J. Thorac Cardiovasc. Surg. 2000, 119: 368-375.
Libby, J. Mol. Cell. Cardiol. 1984. 16: 803-811.
Liechty et al., Nat. Med. 2000, 6: 1282-1286.
Makino et al., J. Clin. Invest. 1999, 103: 697-705.
Mandarim-de-Lacerda and L. M. M. Pereira, Pathobiology, 2000, 68: 36-42.
Marx et al., J. Clin. Invest. 1994, 93: 131-139.
Mezey et al., Science, 2000, 290: 1779-1782.
Mohamed et al., In Vitro Cell and Develop. Biol. 1983. 19: 471-478.
Orlic et al., Ann. N.Y. Acad. Sci., 2001, 938: 221-229.
Orlic et al., Nature, 2001, 410: 701-705.

(Continued)

*Primary Examiner* — Allison Ford
*Assistant Examiner* — Susan E Fernandez
(74) *Attorney, Agent, or Firm* — Brenda Herschbach Jarrell; Choate, Hall & Stewart LLP

(57) ABSTRACT

The present invention provides new methods for the in vitro preparation of bioartificial tissue equivalents and their enhanced integration after implantation in vivo. These methods include submitting a tissue construct to a biomimetic electrical stimulation during cultivation in vitro to improve its structural and functional properties, and/or in vivo, after implantation of the construct, to enhance its integration with host tissue and increase cell survival and functionality. The inventive methods are particularly useful for the production of bioartificial equivalents and/or the repair and replacement of native tissues that contain electrically excitable cells and are subject to electrical stimulation in vivo, such as, for example, cardiac muscle tissue, striated skeletal muscle tissue, smooth muscle tissue, bone, vasculature, and nerve tissue.

45 Claims, 11 Drawing Sheets

OTHER PUBLICATIONS

Orlic et al., Proc. Natl. Acad. Sci. USA, 2001, 98: 10344-10349.
Page and C. K. Manjunath, The Heart and the Cardiovascular System, H. Fozzard et al. (Eds.), Raven: N.Y., 1986, pp. 573-600.
Papadaki et al., Am. J. Physiol. Heart Circ. Physiol. 2001, 280: H168-H178.
Petersen et al., Science, 1998, 284: 1168-1170.
Pittenger et al., Science, 1999, 284: 143-147.
Prockop et al., Science, 1997, 276: 71-74.
Radisic et al., Biotechnol. Bioeng. 2003, 82: 403-414.
Rickard et al., Dev. Biol. 1994, 161: 218-228.
Robinson et al., Cell Transplant, 1996, 5: 77-91.
Sanchez-Ramos, J. Neuroscience Res. 2002, 69: 880-893.
Sankar et al., J. Clin. Invest. 1996, 97: 1436-1446.
Schatteman et al., J. Clin. Invest. 2000, 106: 571-578.
Shi et al., Blood, 1998, 92: 362-367.
Steinhelper et al., Am. J. Physiol. 1990, 259: H1826-H1834.
Suzuki et al., FEBS Letters, 1990, 268: 149-151.
Suzuki et al., J. Cardiov. Pharmacol. 1991, 17: S182-S186.
Suzuki et al., J. Mol. Cell. Cardiol. 1997, 29: 2087-2093.
Theise et al., Hepatology, 2000, 31: 235-240.
Theise et al., Hepatology, 2000, 32: 11-16.
Umezawa et al., J. Cell. Physiol. 1992, 151: 197-205.
Van Kempen et al., Cardiovasc. Res. 1996, 32: 2195-2200.
Wakitani et al., Muscle Nerve, 1995, 18: 1417-1426.
Woodbury et al., J. Neurosci. Res. 2000, 61: 364-370.
Zimmermann et al., Biotechnol. Bioeng. 2000, 68: 106-114.
International Search Report, PCT/US04/19731, date of mailing Oct. 7, 2008.
Written Opinion of the International Searching Authority, PCT/US04/19731, date of mailing Oct. 7, 2008.

* cited by examiner

APPLICATION OF ELECTRICAL STIMULATION FOR FUNCTIONAL TISSUE ENGINEERING IN VITRO AND IN VIVO

This application claims priority from U.S. Provisional Application No. 60/480,214, filed Jun. 20, 2003, the entire contents of which are incorporated herein by reference. To the extent that the incorporated contents conflict with this application, this application shall prevail.

GOVERNMENT INTERESTS

The work described herein was partly supported by the National Aeronautics and Space Administration (NASA, Grant No. NCC8-174). The United States government may have certain rights in the invention.

BACKGROUND OF THE INVENTION

Cardiovascular diseases are responsible for a preponderance of health problems in the majority of the developed countries as well as in many developing countries. Heart disease and stroke, the principal components of cardiovascular disease, are the first and third leading cause of mortality in the U.S., accounting for nearly 40% of all deaths (*Heart and Stroke Statistical Update*, American Heart Association 2002). Cardiovascular diseases also include congenital heart defects, which occur in about 1% of live births (R. F. Gillum, Am. Heart J. 1994, 127: 919-927) and are the main cause of mortality in the first year of life (J. L. Hoffman, Pediatr. Cardiol. 1995, 16: 103-113 and 115-165). When they do not lead to death, cardiovascular diseases may alternatively result in substantial disability and loss of productivity. About 61 million Americans (almost one-fourth of the population) live with cardiovascular disorders, such as coronary heart disease, congenital cardiovascular defects, and congestive heart failure. In 2001, 298.2 billion dollars were spent in the treatment of these clinical conditions, and the economic impact of cardiovascular disease on the U.S. health care system is expected to grow as the population ages.

Over the past 30 years, advances in the treatment and prevention of cardiac diseases have led to constantly declining morbidity and mortality rates. Treatments for both congenital heart defects and cardiomyopathies have become more sophisticated. However, when these treatments fail, organ or tissue replacement remains the only other possible option. Different surgical procedures may be performed to treat heart failure and cardiac deficiency. These procedures include transplantation of organs from one individual to another, reconstructive surgery, and implantation of mechanical devices such as mechanical heart valves.

Cardiac transplantation is so common that the primary limitation on patient outcome is not the surgical technique, but the declining availability of donor organs. In 2000, 2,500 heart transplants were performed in the U.S. while it was estimated that between 20,000 and 40,000 patients could have benefited from such a medical operation. To circumvent the problem of donor organ scarcity, one can resort to surgical reconstruction, whereby damaged or defective tissue at one site of the patient is replaced by healthy tissue from another part of the patient's body. These autografts include blood vessel grafts for heart bypass surgeries. The disadvantages of using autografts are their limited durability (E. Braunwald, *Heart Disease* 4$^{th}$ Edition, E. Braunwald (Ed.), W. B. Saunders: Philadelphia, Pa., 1992, pp. 1007-1077) and a loss of function at the donor site. In addition, reconstructive surgery often involves using the body's tissues for purposes not originally intended, which can result in long-term complications. Mechanical heart valve prostheses have proved to effectively improve patient's quality of life. However, they are also subject to mechanical failure and rejection, can induce inflammation and/or infection, and require long-term drug intervention to prevent blood-clotting. Furthermore, since these mechanical valve substitutes are nonviable, they have no potential to grow, to repair or to remodel; therefore their durability is limited, especially in growing children (J. E. Mayer Jr., Semin. Thorac. Cardiovasc. Surg. 1995, 7: 130-132). Since currently available treatments (with the exception of cardiac transplantation) are only palliative, new drugs and procedures for treating cardiovascular diseases, especially approaches allowing the recovery of diminished cardiac function, are highly desirable.

Tissue engineering is emerging as a significant potential alternative or complementary solution. In tissue engineering, tissue or organ failure is addressed by implanting natural, synthetic, or semi-synthetic tissue and organ mimics that are fully functional from the start or that grow into the required functionality to replace, repair, maintain and/or enhance organ/tissue function. Although efforts to generate bioartificial tissues and organs for human therapies go back at least thirty years, such efforts have come closer to clinical success only in the last ten years. In addition to developing improved bioartificial tissue equivalents for therapeutic purposes as well as for in vitro research and drug development, tissue engineering also aims at providing measures to enhance survival and integration of engineered grafts following implantation in vivo.

One of the major strategies adopted for the creation of engineered tissues is the in vitro growth of isolated cells on three-dimensional templates or scaffolds under conditions that coax the cells to develop into a functional tissue. The scaffolds, which can be fashioned from synthetic polymers or from natural materials such as collagen, temporarily provide the biomechanical support needed by the cells. As the cells grow and differentiate on the scaffold, they produce their own extracellular matrix. When implanted, the bioartificial tissue should become structurally and functionally integrated into the body.

The feasibility of engineered functional cardiac muscle has been demonstrated (T. Eschenhagen et al., FASEB J. 1997, 11: 683-694; L. E. Freed and G. Vunjak-Novakovic, In Vitro Cell Dev. Biol. 1997, 33: 381-385; R. Akins et al., Tissue Eng. 1999, 5: 103-118; N. Bursac et al., Am. J. Physiol. Heart Circ. Physiol. 1999, 277: H433-H444; R. L. Carrier et al., Biotechnol. Bioeng. 1999, 64: 580-589). Eschenhagen and co-workers (T. Eschenhagen et al., FASEB J. 1997, 11: 683-694) showed that embryonic chick cardiac myocytes cultured in collagen gels displayed characteristic physiological responses to physical and pharmacological stimuli; and Akins et al. (R. Akins et al., Tissue Eng. 1999, 5: 103-118) demonstrated that rat ventricular cardiomyocytes cultured on polystyrene microcarrier beads in bioreactors formed three-dimensional spontaneously contractile aggregates. Cultivation of neonatal rat cardiac myocytes on polyglycolic scaffolds in bioreactors has been shown to result in contractile three-dimensional tissues (L. E. Freed and G. Vunjak-Novakovic, In Vitro Cell Dev. Biol. 1997, 33: 381-385) with ultrastructural features of cardiac muscle (N. Bursac et al., Am. J. Physiol. Heart Circ. Physiol. 1999, 277: H433-H444). These studies also provided evidence that variations in initial cell density and cultivation conditions affect the structure of the engineered cardiac tissue produced (R. L. Carrier et al., Biotechnol. Bioeng. 1999, 64: 580-589; M. Papadaki et al., Am. J. Physiol. Heart Circ. Physiol. 2001, 280: H168-H178).

One of the major difficulties in engineering a functional cardiac tissue starting from isolated cells is the heart's complex structure and function at different spatial scales. The complex structure of the heart stems from the elongation and spatial alignment of cardiac myocytes, from the distribution of intercellular connections, and from the formation of cardiac muscle fibers and bundles that rotate transmurally inside the heart wall. This unique architecture of cardiac tissue enables an orderly sequence of electrical and mechanical activity and efficient pumping of blood from the heart. Unsurprisingly, the intricate arrangement and geometrical order of different cell types in living cardiac muscle tissue is difficult to reproduce in vitro; and standard tissue engineering culture of cardiac muscle cells seldom yields tissue of such complex structure.

Indeed, most tissue engineering techniques used so far have led to cardiac muscle constructs with a number of shortcomings that limit their usefulness for both in vitro and in vivo applications. Most often, unlike native cardiac muscle that consists of fibers with a defined orientation, the cells in engineered constructs exhibit random orientation and a poor degree of differentiation. Furthermore, the constructs often present a non-uniform spatial cell distribution with, for example, a good tissue formation at the periphery and a loose network of disoriented cells at the center of the construct. Since only a minor fraction of the three-dimensional structure consists of cardiac tissue, its usefulness as a medical implant for replacement therapy is limited. Furthermore, it is generally recognized that structural and functional integration of engineered grafts remains unsolved. Even if high-fidelity engineered tissue equivalents become available, the process of integration will need to be enhanced for the tissue graft to survive implantation and remain functional.

Therefore, a need continues to exist for new strategies that offer novel and satisfactory platforms for in vitro research and the eventual development of compact, thick and functional transplantable heart muscle. In particular, methods for the production of three-dimensional bioartificial constructs with properties resembling those of native cardiac tissue are highly desirable, as are methods allowing their enhanced integration and functionality in vivo.

SUMMARY OF THE INVENTION

The present invention is directed to improved systems for the development of bioartificial tissues in vitro and their integration with host tissues following implantation in vivo. More specifically, the present invention provides strategies that (a) allow the formation of three-dimensional tissue-engineered constructs having structural and functional characteristics of a native tissue, and that (b) enhance the integration of engineered and host tissues following implantation of the construct in vivo. The invention further provides three-dimensional tissue-engineered constructs that can be used as bioartificial tissue equivalents for in vitro research and/or as medical implants for the repair and replacement of deficient or damaged natural structure(s).

In one aspect, the present invention provides preparation methods of three-dimensional tissue-engineered constructs. More specifically, the inventive methods comprise contacting an appropriate substrate with mammalian cells to form a cell-seeded construct, and cultivating the resulting cell-seeded construct in the presence of a biomimetic electrical stimulation. The cultivation is carried out under conditions and for a time period that allow the formation of a three-dimensional cell structure having structural and functional characteristics of a native tissue. Preferably, the native tissue is one that contains electrically excitable cells and is subject to electrical stimulation in vivo, such as, for example, cardiac muscle tissue, striated skeletal muscle tissue, smooth muscle tissue, bone, vasculature, or nerve tissue.

Cultivating the cell-seeded construct may include implanting the cell-seeded construct in vivo and placing the cell-seeded construct in electrical communication with a source of biomimetic electrical stimulation. The method may further include cultivating the cell-seeded construct in perfusion. The cell-seeded construct may be cultivated in perfusion in the presence of the biomimetic electrical stimulation.

In some embodiments, the substrate used in the preparative methods is biocompatible. This is particularly important when the three-dimensional tissue-engineered construct produced is to be implanted in a patient. Depending on the intended purpose of the construct, the substrate may be biodegradable or non-biodegradable; it may comprise a naturally-occurring polymer, a synthetic polymer, or any combination of naturally-occurring and/or synthetic polymers. The substrate may have a dry thickness of at least 1.5 mm.

In certain embodiments, the mammalian cells used in the preparative methods of the invention comprise cells of one cell type. In other embodiments, mammalian cells are of at least two different cell types. Suitable mammalian cells include neonatal cells, adult or aged cells, progenitor cells, genetically transformed cells, adult stem cells, mesenchymal stem cells, and embryonic stem cells. In still other embodiments, the mammalian cells are human cells.

For example, when the inventive methods of preparation are applied to produce a three-dimensional tissue-engineered cardiac muscle construct, the mammalian cells may be selected from the group consisting of cardiomyocytes, endocardial cells, cardiac adrenergic cells, cardiac fibroblasts, vascular endothelial cells, smooth muscle cells, cardiac progenitor cells, adult stem cells, mesenchymal stem cells, embryonic stem cells, and combinations of these. In certain embodiments, the inventive preparation methods further comprise the step of harvesting mammalian cells from an individual and cultivating these cells in vitro before contacting the substrate. When the construct is intended to be used as a medical implant, the mammalian cells may be of autologous and/or heterologous origin.

In other embodiments, the cultivation of the cell-seeded construct is carried out under conditions selected to promote deposition of extracellular matrix components. The cultivation of the cell-seeded construct may also be carried out under conditions that promote cell proliferation and/or cell differentiation. Alternatively or additionally, the cultivation may be carried out under conditions and for a time period such that they allow the formation of a three-dimensional construct with a pre-determined thickness. The cultivation conditions may also be chosen to stimulate the formation of a three-dimensional construct, wherein the cells are organized on the substrate with a defined orientation.

The cell-seeded construct is cultivated in the presence of an electrical stimulation that mimics the electrical stimulation received by a specific native tissue in vivo. For example, the production of a three-dimensional tissue-engineered cardiac muscle construct using the inventive methods comprises cultivation of the cell-seeded construct in the presence of an electrical stimulation that mimics the electrical stimulation received by a cardiac muscle tissue in vivo. Furthermore, when the mammalian cells are cardiac progenitor cells and/or stem cells, the cardiac-like electrical stimulation is used to induce their differentiation into cardiac myocytes.

The electrical stimulation used to produce a tissue-engineered construct may alternatively be chosen to mimic the electrical stimulation received by a striated skeletal muscle tissue, smooth muscle tissue, bone, vasculature, or nerve tissue in vivo.

In other embodiments, the inventive methods further comprise the step of stimulating the cell-seeded construct mechanically and/or chemically.

In still other embodiments, the inventive preparation methods further comprise the step of treating the three-dimensional tissue-engineered construct with at least one biologically active agent. The biologically active agent may be selected from the group consisting of growth factors, adhesion factors, soluble extracellular matrix proteins, antibiotics, agents that enhance vascularization, agents that enhance cell differentiation, agents that enhance tissue differentiation, agents that inhibit fibrosis, agents that inhibit tumorigenesis, agents that enhance cell proliferation, agents that inhibit cell proliferation, agents that inhibit scaffold degradation, agents that enhance scaffold degradation, agents that enhance histocompatibility, and agents that enhance hemocompatibility.

Steps of submitting the three-dimensional tissue-engineered construct to further tissue engineering and/or of storing the three-dimensional tissue-engineered construct after preparation by the inventive methods are also intended to be within the scope of the present invention.

In another aspect, the present invention is directed to tissue-engineered constructs comprising mammalian cells organized on a substrate to provide a three-dimensional cell structure having structural and functional characteristics of a native tissue, wherein the three-dimensional cell structure is obtained by contacting the substrate with mammalian cells to form a cell-seeded construct, and cultivating the resulting cell-seeded construct in the presence of a biomimetic electrical stimulation. Substrates and mammalian cells suitable for the production of the inventive three-dimensional tissue constructs are as described above.

In certain embodiments, the inventive constructs have structural and functional characteristics of a native tissue that contains electrically excitable cells and is subject to electrical stimulation in vivo, such as cardiac muscle tissue, striated skeletal muscle tissue, smooth muscle tissue, bone, vasculature, or nerve tissue.

In still other embodiments, the inventive constructs may further comprise extracellular matrix components, such as fibronectin, collagen type IV, collagen type I, laminin, thrombospondin, vibronectin, proteoglycans, hyaluronan, and nidogen. Additionally or alternatively, the cells on the substrate may be organized with a defined orientation. In yet other embodiments, the inventive three-dimensional tissue-engineered constructs may further comprise at least one biologically active agent, as listed above.

In another aspect, the present invention provides methods for treating an individual suffering from tissue deficiency, damage or loss. These methods include producing a three-dimensional tissue-engineered construct according to the preparation methods described above; implanting the construct into the individual in need thereof; and submitting the implanted construct to a biomimetic electrical stimulation. The electrical stimulation may enhance integration of the implanted construct with host tissue, and/or may increase cell survival and/or cell functionality in vivo. The construct to be implanted may further comprise at least one biologically active agent, and thereby serve as vehicle for delivery of the biologically active agent(s) to the individual. The inventive methods of treatment are particularly useful when the tissue to be replaced or supplemented is one that is subject to electrical stimulation in vivo. The inventive methods may, for example, be applied for treating an individual suffering from tissue deficiency, damage or loss associated with a congenital heart disease or with an acquired heart disease.

In yet another aspect, the invention provides methods for testing three-dimensional tissue-engineered constructs in vitro. These methods comprise producing a construct according to the preparative methods described above, exposing the construct to a test factor, and observing a response of the construct to the test factor.

Suitable test factors include, but are not limited to, mechanical stimulus, electrical stimulus, temperature, pH, gas content, oxygen concentration, inorganic molecules, organic molecules, biologically active agents (such as those listed above), plant extracts, drugs, and potential therapeutic candidates.

In certain embodiments, observing the response of the construct to the test factor comprises studying or assessing at least one property of the construct. The properties of the construct that can be studied or assessed include, for example, strength, elasticity, durability, conductivity, contractility, tissue organization, cellular organization, cell viability, cell morphology, metabolic activity, cell cycle progression, fraction of apoptotic cells, ultrastructural features, electrical signal propagation, gene expression, and protein expression. Different methods may be used to observe the response of the construct to the test factor.

Other aspects, features and advantages of the present invention will become apparent from the following detailed description. It should be understood, however, that the detailed description and specific examples, while indicating preferred embodiments of the invention, are given by way of illustration only.

BRIEF DESCRIPTION OF THE DRAWING

The patent or application file contains at least one drawing executed in color. Copies of this patent or patent application publication with color drawings will be provided by the Office upon request and payment of the necessary fee.

DEFINITIONS

Figure 1B:
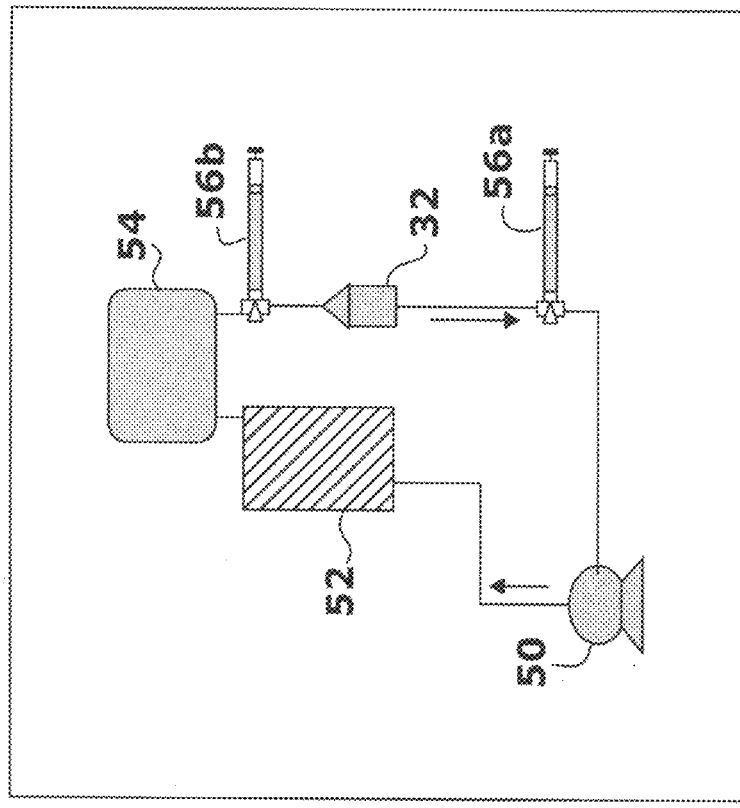
FIG. 1B is a schematic diagram of a perfusion system for culturing constructs according to an embodiment of the invention.

The terms "engineered tissue/construct", "tissue-engineered construct", and "bioartificial tissue/construct" are used herein interchangeably. They refer to a tissue or organ that is produced, in whole or in part, using tissue engineering techniques. Exemplary descriptions of these techniques have been published (see, for example, "*Principles of Tissue Engineering, 2nd Edition*", R. Lanza, R. Langer, and J. Vacanti (Eds.), Academic Press, 2000; "*Methods of Tissue Engineering*", A. Atala and R. Lanza (Eds.), Academic Press, 2001; "*Animal Cell Culture*", Masters (Ed.), Oxford University Press: New York, 2000; U.S. Pat. No. 4,963,489 and related U.S. patents).

The term "biomimetic electrical stimulation", as used herein, refers to an electrical stimulus that is applied to a tissue construct either in vitro (during cultivation and formation of the construct) or in vivo (following implantation of the construct into an individual in need thereof). The electrical stimulation applied to the tissue-engineered construct is such that it resembles the electrical stimulation received by a specific native tissue in vivo. For example, cardiac tissue constructs of the invention may be cultivated in the presence of an electrical stimulation that mimics the electrical stimulation received by a cardiac muscle tissue in vivo.

As used herein, the term "structural and functional characteristics of a native tissue" refers to the anatomical (structural) and physiological (functional) characteristics exhibited by a construct that resemble the properties of an intact (i.e., not damaged, failing or deficient) native tissue in vivo. These properties include three-dimensional organization as well as physiological functions and responses.

The term "treatment" is used herein to characterize a method that is aimed at (1) delaying or preventing the onset of a medical condition; or (2) slowing down or stopping the progression, aggravation, or deterioration of the symptoms of the condition; or (3) bringing about ameliorations of the symptoms of the condition; and/or (4) curing the condition. The treatment may be administered prior to the onset of the disease, for a prophylactic or preventive action. It may also be administered after initiation of the disease, for a therapeutic action.

The terms "individual" and "patient" are used herein interchangeably. They refer to a human or another mammal, that suffers from tissue deficiency, damage or loss. In one embodiment, the deficiency, damage and/or loss affect(s) a native tissue that contains electrically excitable cells and is subject to electrical stimulation in vivo.

The term "implantation" refers to the medical operation by which an organ, group of cells, mechanical device or bioartificial tissue construct is put into the body of an individual.

The term "integration", as used herein, refers to a direct functional and structural connection between native host tissue and implanted engineered construct(s).

The term "histocompatibility" refers to the degree of similarity between the histocompatibility antigens of two individuals. Histocompatibility determines whether an organ transplant or engineered construct implant will be tolerated or rejected by the recipient's body.

As used herein, the term "hemocompatibility" refers to the ability of any material, mechanical device or tissue-engineered construct to be in contact with blood without interacting with any blood components so as to cause their inappropriate activation or destruction. Hemocompatible medical devices or materials do not trigger adverse reactions such as platelet attachment, platelet activation, and complement activation that eventually lead to fibrin production and clot formation. Agents that enhance hemocompatibility include, but are not limited to, anticoagulants such as heparin and warfarin.

The term "biocompatible", as used herein, is intended to describe any material which upon implantation does not provoke an undesirable adverse response in the patient (i.e., an undesirable reaction other than the expected response to the trauma of implantation). When introduced into a patient, a biocompatible material is not toxic or harmful to that patient, and does not cause immunological rejection.

The term "biodegradable", as used herein, refers to the ability of materials to degrade under physiological conditions to form a product that can be metabolized or excreted without damage to organs. Biodegradable materials are not necessarily hydrolytically degradable and may require enzymatic action to fully degrade. Biodegradable materials also include materials that are broken down in cells.

The term "extracellular matrix" refers to a complex, three-dimensional network of macromolecules (such as proteins) that provides an architectural scaffold for cellular adhesion and migration.

In the context of the present invention, cells are organized on a substrate "with a defined orientation" when their spatial organization on the substrate is non-random.

The term "gap junction", as used herein, refers to a junction between two cells, which consists of pores that allow the passage of small molecules (up to 9 kDa) from the cytoplasm of one cell to the cytoplasm of another cell.

The term "connexin" refers to the main protein component of a connexon, the structural subunit of a gap junction (six connexins make up one connexon).

The term "cell proliferation" refers to an expansion of a population of cells by the continuous division of single cells into two identical daughter cells.

The term "cell differentiation", as used herein, refers to the elaboration of particular characteristics that are expressed by an end-stage cell type or a cell en route to becoming an end-stage cell (i.e., a specialized cell). The term "directed differentiation" refers to a process of manipulating cell culture conditions to induce differentiation into a particular cell type. The term "cell trans-differentiation" refers to the process by which a cell changes from one state of differentiation to another.

The term "stem cell" refers to a relatively undifferentiated cell that has the capacity for sustained self-renewal, often throughout the lifetime of an animal or human, as well as the potential to give rise to differentiated progeny (i.e., to different types of specialized cells). An "embryonic stem cell" is a stem cell derived from a group of cells called the inner cell mass, which is part of the early (4 to 5 days old) embryo called the blastocyst. Once removed from the blastocyst, the cells of the inner cell mass can be cultured into embryonic stem cells. In the laboratory, embryonic stem cells can proliferate indefinitely, a property that is not shared by adult stem cells. An "adult stem cell" is an undifferentiated cell found in a differentiated (specialized) tissue. Adult stem cells are capable of making identical copies of themselves for the lifetime of the organism. Adult stem cells usually divide to generate progenitor or precursor cells, which then differentiate or develop into "mature" cell types that have characteristic shapes and specialized functions. Sources of adult stem cells include bone marrow, blood, the cornea and retina of the eye, brain, skeletal muscle, dental pulp, liver, skin, the lining of the gastrointestinal tract, and pancreas.

The term "pluripotent stem cell" refers to a stem cell that has the ability to give rise to types of cells that develop from the three germ layers (mesoderm, endoderm, and ectoderm) from which all the cells of the body arise.

The term "plasticity" refers to the ability of an adult stem cell from one tissue to generate the specialized cell type(s) of another tissue.

The terms "progenitor cell" or "precursor cell" are used herein interchangeably. They refer to a cell that occurs in fetal or adult tissue and is partially specialized; it divides and gives rise to differentiated cells. Precursor cells belong to a transitory amplifying population of cells derived from stem cells. Progenitor cells do not have the capacity for sustained, undifferentiated self-renewal.

Additional definitions are provided throughout the Detailed Description.

DETAILED DESCRIPTION OF CERTAIN PREFERRED EMBODIMENTS

The present invention is directed to improved strategies for the creation of bioartificial tissues. More specifically, systems are described that allow for the formation of three-dimensional tissue-engineered constructs having structural and functional characteristics of a native tissue. In particular, the invention provides preparation methods for the production of bioartificial equivalents of native tissues that contain electrically excitable cells and are subject to electrical stimulation in vivo. Examples of such native tissues include cardiac muscle tissue, striated skeletal muscle tissue, smooth muscle tissue, bone, vasculature, and nerve tissue.

I. Preparative Methods of Three-dimensional Tissue-engineered Constructs

In one aspect, the present invention provides preparation methods for three-dimensional tissue-engineered constructs which include the steps of contacting a suitable substrate with mammalian cells to form a cell-seeded construct, and cultivating the resulting cell-seeded construct in vitro in the presence of a biomimetic electrical stimulation. The in vitro cultivation is carried out under conditions and for a time period such that they allow the formation of a three-dimensional cell structure, which exhibits structural and functional characteristics of a native tissue.

Substrate

As mentioned above, cells placed in culture typically adopt a two-dimensional monolayer configuration that is random, disordered and different from that of cells within a native tissue. In tissue engineering techniques, a substrate is used to stimulate a more in vivo-like organization of the cells and facilitate the creation of new functional tissue in three dimensions. More specifically, substrates serve as templates to which seeded cells can attach or adhere and provide the cells with the biomechanical support they initially need to grow, differentiate, produce their own extracellular matrix, and organize into three-dimensional structures representative of native tissue.

To facilitate cell metabolism, the substrate may include a porous three-dimensional scaffold including an interconnected pore network for cell/tissue growth and flow transport of nutrients, oxygen and metabolic waste. The substrate should be compatible with the types of cells that are used in the preparation of the construct and should exhibit a suitable surface chemistry for cell attachment, proliferation and/or differentiation. Substrate materials that are easily processed will allow the formation of a variety of shapes and sizes.

The selection of a substrate for use in the preparative methods of the invention will depend on the intended purpose of the tissue-engineered construct. Different properties of the support material may be considered. These properties include, but are not limited to, biocompatibility, biodegradability, tensile strength, flexibility, elasticity, and cost. For example, when the engineered construct is intended to be used as a medical implant, the material should be biologically compatible for implantation into an individual. Furthermore, the substrate may display mechanical properties that match those of the native tissues at the site of implantation. Additionally or alternatively, it may be desirable to control the degradation and resorption rate of the support material to match cell/tissue growth in vitro and/or in vivo. Similarly, the size and geometry of the substrate, which will directly influence the dimensions and shape of the final engineered construct, will be selected based on the intended use of the construct. Substrates in the form of a mesh, foam, gel, sponge, suture and the like have routinely been used in tissue engineering.

Suitable substrates for use in the practice of the preparative methods of the present invention may include a naturally-occurring polymer, a synthetic polymer, or a combination of natural and/or synthetic polymers.

Naturally-occurring polymers include polysaccharides and proteins. Exemplary polysaccharides include starches, dextrans, celluloses, hyaluronic acid and its derivatives; exemplary proteins include collagen and gelatin. Polysaccharides such as starches, dextrans, and celluloses may be unmodified or may be modified physically or chemically to affect one or more of their properties such as their characteristics in the hydrated state, their solubility, or their half-life in vivo.

In certain embodiments, the substrate includes a biocompatible, degradable polymer. Such polymers can be broken down by cellular action and/or by action of non-living body fluid components. A variety of biocompatible, degradable polymers are suitable for use in the preparation methods of the present invention. These include, but are not limited to, polyanhydrides, polyorthoesters, polyphosphazenes, polycaprolactones, polyamides, polyurethanes, polyesteramides, polydioxanones, polyacetals, polyketals, polycarbonates, polyorthocarbonates, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or higher poly-monomer polymers thereof, or combinations or mixtures thereof.

In other embodiments, the polymer includes polyhydroxy acids such as polylactic acid (PLA), polyglycolic acid (PGA), their copolymers poly(lactic-co-glycolic acid) (PLAGA), and mixtures of any of these. These polymers are among the synthetic polymers approved for human clinical use as surgical suture materials and in controlled release devices. They are degraded by hydrolysis to products that can be metabolized and excreted. Furthermore, copolymerization of PLA and PGA offers the advantage of a large spectrum of degradation rates from a few days to several years by simply varying the copolymer ratio of glycolic acid to lactic acid which is more hydrophobic and less crystalline than PGA and degrades at a slower rate.

Mammalian Cells

Suitable mammalian cells for use with the inventive methods of preparation of three-dimensional tissue-engineered constructs are cells that have a native capacity for differentiation into a particular tissue or cells that may be manipulated into forming a particular tissue. Therefore, suitable mammalian cells include neonatal cells, autologous or heterologous adult or aged donor cells, progenitor or precursor cells, and stem cells as long as they can be manipulated to form a given tissue. In one embodiment, the mammalian cells are (or can become, for example, after differentiation) electrically excitable.

Exemplary mammalian cells for use with the preparative methods of the present invention include mouse, rat, rabbit, guinea pig, hamster, cow, pig, horse, goat, sheep, dog, cat and human cells. The cellular composition used in the preparation may be varied depending on the intended purpose of the three-dimensional tissue-engineered construct. In certain embodiments, the mammalian cells are of a single cell type. In other embodiments, the mammalian cells are of at least two different cell types. For example, a cardiac muscle construct may be made up of cardiac myocytes only. Alternatively, myocardial cells, endocardial cells, vascular smooth muscle cells, vascular endothelium, fibroblasts, and adrenergic cells, or various subsets of those cell types may be co-cultured and used to prepare an organotypic structure resembling cardiac tissue. In addition, the mammalian cells used in the production of the construct may come from a single individual, from different individuals of the same species, or different individuals of different species. The cells may also be genetically engineered to, for example, contain a gene of interest such as a gene expressing a growth factor.

Tissue precursor cells can be obtained directly from a patient, from a culture of cells from a donor, or from established cell culture lines.

Examples of established cell lines that can be used in the preparation of electrically excitable tissue constructs include, but are not limited to, HL-1, AT-1, PC12, and C2C12 cells. C2C12 cells were originally derived from skeletal myoblasts (satellite cells, S. W. Robinsong et al., Cell Transplant, 1996, 5: 77-91) and are known to be able to trans-differentiate, acquiring characteristics of cardiac myocytes, such as the expression of connexin-43 (the major protein of cardiac gap junctions) and the formation of desmosomes at cell junctions. The PC12 rat pheochromocytoma cell line is widely used to study neuronal differentiation by growth factors. In response to nerve growth factors and basic fibroblast growth factors, PC 12 cells acquire the phenotype of mature sympathetic neurons and become electrically excitable. HL-1 cells, derived from a mouse atrial cardiomyocyte tumor, are able to proliferate and can be serially passaged while retaining the phenotypic characteristics of the adult cardiomyocytes (W. C. Claycomb et al., Proc. Natl. Acad. Sci. USA, 1998, 95: 2979-2984). AT-1 cells are a transplantable tumor lineage derived from transgenic mouse atrial cardiomyocytes (M. E. Steinhelper et al., Am. J. Physiol. 1990, 259: H1826-H1834). These cells have the capacity to divide in culture and maintain a highly differentiated cardiac phenotype. More specifically, cultured AT-1 cells express adult cardiac-specific proteins ($\alpha$-myosin heavy chain and sarcomeric $\alpha$-actin) and connexin 43, they exhibit ultrastructural features of cardiomyocytes (such as sarcomers, transverse tubules, and intercalated disks), and they have characteristic cardiac electrophysiological properties. All these cell lines are of animal origin.

Suitable mammalian cells for use with the preparative methods of the invention may alternatively be obtained from the patient to be treated or from a donor. Ideally, when the construct is to be used as a medical implant, a biopsy of the patient's own tissue is obtained. Cells can be isolated from a healthy tissue adjacent defective tissue, or from other sites of healthy tissue in the patient. For example, precursor cells from healthy section of a heart that has been damaged or is deficient may be harvested. The construct formed using these harvested cells may then be introduced to the damaged/defective area of the patient's heart via implantation. Alternatively, or in addition, mesenchymal stem cells may be harvested from a patient's or a donor's bone marrow. The main advantage of autologous cells is that they do not elicit an immunologic reaction in the patient. Alternatively, when the use of autologous cells is not feasible, cells of the same species and preferably of the same immunological profile can be obtained by biopsy, for example, from a patient's close relative.

Heterologous cells can be obtained from donor organs. Donor tissue from individual biopsies, surgical remnants, or whole donor organs can be used as cell sources for the preparation of tissue constructs. This procedure allows the generation of a large number of constructs using cells from a single donor, and therefore significantly decreases the demand for donor organs. However, heterologous cells may elicit an immune reaction in the recipient and require that the patient be immunosuppressed. Although immunosuppression can easily be achieved, for example, by using a schedule of steroids and other immunosuppressant drugs such as cyclosporine, it is known to have many adverse side effects.

The cells harvested from donors are grown in culture using standard cell techniques and conditions, and are utilized when needed. Except for cardiac myocytes, which have limited proliferation potential, cells are cultured only until a sufficient number of cells have been obtained for a particular application. Cells from biopsies are harvested, cultured, and then isolated, pre-plated or selected using specific markers to remove undesired cells types.

Cell viability can be determined using standard techniques including histology, quantitative assessment with radioisotopes, or visual observation using a light or scanning electron microscope or a fluorescent microscope. The biological function of the cells delivered to the support structure can be determined using a combination of the above techniques and standard functional assays.

Different cell types may be harvested from a patient or a donor. For example, when the inventive preparative methods are applied to produce a three-dimensional tissue-engineered cardiac muscle construct, the mammalian cells may include cardiomyocytes, endocardial cells, cardiac adrenergic cells, cardiac fibroblasts, vascular endothelial cells, smooth muscle cells, and combinations of any of these.

Alternatively, stem cells, which can provide a virtually never-ending supply of cells for tissue engineering, may be used in the preparative methods of the invention. The advantage of embryonic stem cells as a cell source, include virtually indefinite growth and differentiation potential that encompasses all cells and tissues. Specific differentiation in vitro into cells with the phenotypic characteristics of cardiomyocytes, neural cells, insulin producing beta cells, and hematopoietic cells has been demonstrated.

The discovery that some stem cell populations isolated from adult tissues exhibit some degree of plasticity has opened new avenues for basic biological research and the development of novel therapies and clinical tools. The so-called adult stem cells can be derived from a variety of specific tissues to provide, for example, mesenchymal, neuronal and endothelial stem cells.

There has been a plethora of reports suggesting that primitive stem cells within whole bone marrow possess greater functional plasticity than was previously suspected. After bone marrow transplantation into animals, donor-derived stem cells have been found in such diverse non-hematopoietic tissues as skeletal muscle (G. Ferrari et al., Science, 1998, 279: 1528-1530), cardiac muscle (R. E. Bittner et al., Anat. Embryol. 1999, 199: 391-396), liver (B. E. Petersen et al., Science, 1999, 284: 1168-1170; E. Lagasse et al., Nat. Med. 2000, 6: 1229-1234; B. E. Petersen et al., Science, 1998, 284: 1168-1170; N. D. Theise et al., Hepatology, 2000, 31: 1235-1240; N. D. Theise et al., Hepatology, 2000, 32: 11-16), vascular endothelium (T. Asahara et al., Science, 1997, 275: 964-967; G. C. Schatteman et al., J. Clin. Invest. 2000, 106: 571-578; Q. Shi et al., Blood, 1998, 92: 362-367) and brain (E. Mezey et al., Science, 2000, 290: 1779-1782; T. R. Brazelton et al., Science, 2000, 290: 1775-1779; M. A. Eglitis and E. Mezey, Proc. Natl. Acad. Sci. USA, 1997, 94: 4080-4085). Similarly, enriched or purified hematopoietic stem cells were reported to generate skeletal muscle (E. Gussoni et al., Nature, 1999, 401: 390-394), cardiac muscle (K. A. Jackson et al., J. Clin. Invest. 2001, 107: 1395-1402; D. Orlic et al., Proc. Natl. Acad. Sci. USA, 2001, 98: 10344-10349; D. Orlic et al., Science, 2001, 410: 701-705), endothelial cells (K. A. Jackson et al., J. Clin. Invest. 2001, 107: 1395-1402), liver hepatocytes and bile duct (E. Lagasse et al., Nat. Med. 2000, 6: 1229-1234), as well as multiple epithelial tissues (D. S. Krause et al., Cell, 2001, 105: 369-377).

Stem cells derived from bone marrow, whether multipotent hematopoietic stem cells or other tissue specific stem cells resident in the bone marrow, have a major advantage over stem cells from other organs: they are well defined and easy to isolate. Moreover, transplantation of bone marrow or hematopoietic stem cells was also found to induce donor tolerance, allowing trans-differentiation or transplantation of other tissue specific stem cells from the same donor without the need for prolonged immunosuppression of the recipient. In addition, cells may be isolated from bone marrow without further injuring healthy tissue near the site being repaired using the techniques described herein.

In particular, mesenchymal stem cells, which reside within the bone marrow cavity, have been shown, both in culture and following injection into particular tissues in mammals, to give rise to a range of cell types including chrondrocytes, osteoblasts, adipocytes, cardiac and skeletal muscle cells (K. W. Liechty et al., Nat. Med. 2000, 6: 1282-1286; M. F. Pittenger et al., Science, 1999, 284: 143-147), as well as cells typical of the central nervous system, such as neurons and astrocytes (G. C. Kopen et al., Proc. Natl. Acad. Sci. USA, 1999, 96: 10711-10716; D. Woodbury et al., J. Neurosci. Res. 2000, 61: 364-370). Isolation, purification and culture expression of human mesenchymal stem cells are described in U.S. Pat. No. 6,387,369.

The microenvironment (including contact with surrounding cells, formation of extracellular matrix, nature of local milieu as well as presence of growth and differentiation factors) plays a role in determining the stem cells' function. Stem cell cultures can be treated under conditions and/or in the presence of specific factors and agents that drive differentiation along a predetermined lineage. A selectable marker under the control of a lineage-specific promoter, for example, a transcription factor that is switched on early during lineage-specific differentiation, may be inserted into the stem cells. The selectable marker will then be expressed in cells undergoing differentiation into the lineage in question, and, by applying the selective agent, it is possible to kill off other cell types in the cultures.

For example, U.S. Pat. No. 6,387,369 describes a series of specific treatments applicable to mesenchymal stem cells to induce expression of cardiac specific genes. The conditions that are disclosed are effective on rat, canine, and human mesenchymal stem cells. Mesenchymal stem cells that progress towards cardiomyocytes first express proteins found in fetal cardiac tissue and then proceed to adult forms. Detection of expression of cardiomyocyte-specific proteins can be achieved by using antibodies to, for example, myosin heavy chain monoclonal antibody MF 20 or sarcoplasmic reticulum calcium ATPase.

Mesenchymal stem cells may also be genetically modified or engineered to express proteins of importance for the differentiation and/or maintenance of striated skeletal muscle cells. Exemplary proteins include growth factors (e.g., TGF-β, IGF-1, FGF), myogenic factors (e.g., myoD, myogenin, Myf5, MRF), transcription factors (e.g., GATA-4), cytokines (e.g., cardiotropin-1), members of the neuregulin family (e.g., neuregulin 1, 2, and 3) and homeobox genes (e.g., Csx, tinman, NKx family).

Other mammalian cells that can be used in the preparation methods of the present invention include precursor cells. Usually, between the stem cell and its terminally differentiated progeny state, there is an intermediate population of committed progenitors with limited proliferative capacity and restricted differentiation potential. These cells, called progenitor or precursor cells, are sometimes known as transit amplifying cells.

Several reports (D. J. Prockop et al., Science, 1997, 276: 71-74; D. J. Rickard et al., Dev. Biol. 1994, 161: 218-228, A. J. Friedenstein et al., Cell Tissue Kinet. 1987, 20: 263-272; G. Ferrari et al., Science, 1998, 279: 1528-1530; A. Umezawa et al., J. Cell. Physiol. 1992, 151: 197-205; B. A. Ashton et al., Clin. Orthop. 1980, 151: 294-307; S. Makino et al., J. Clin. Invest. 1999, 103: 697-705) have, for example, revealed that marrow stromal cells have many characteristics of mesenchymal stem cells. Pluripotential progenitor marrow stromal cells may differentiate into various cell types, including bone (D. J. Rickard et al., Dev. Biol. 1994, 161: 218-228, A. J. Friedenstein et al., Cell Tissue Kinet. 1987, 20: 263-272), muscle (S. Wakitani et al., Muscle Nerve, 1995, 18: 1417-1426; G. Ferrari et al., Science, 1998, 279: 1528-1530), fat (A. Umezawa et al., J. Cell. Physiol. 1992, 151: 197-205), oval hepatocytes (B. E. Petersen et al., Science, 1999, 284: 1168-1170), tendon or cartilage (B. A. Ashton et al., Clin. Orthop. 1980, 151: 294-307), and cardiomyocytes (S. Makino et al., J. Clin. Invest. 1999, 103: 697- 705; D. Orlic et al., Nature, 2001, 938: 221-229).

Progenitor cells that can be used for the preparation of bioartificial equivalents of cardiac muscle tissue, striated skeletal muscle tissue, smooth muscle tissue, bone, vasculature, and nerve tissue are known in the art.

Cultivation of Cell-Seeded Construct

After preparation as described above, mammalian cells are seeded onto a three-dimensional substrate, and the resulting cell-seeded construct is immersed in medium in a culture dish or bioreactor (R. L. Carrier et al., Biotechnol. Bioeng. 1999, 64: 580-589; J. Leor et al., Circulation, 2000, 102: III56-III61; R. K. Li et al., Circulation, 1999, 100: II63-II69; M. Papadaki et al., Am. J. Physiol: Heart Circ. Physiol. 2001, 280: H168-H178).

The in vitro cultivation of cell-seeded substrates may be carried out by any method that leads to the formation of three-dimensional tissue constructs exhibiting properties characteristic of a native tissue. More specifically, the seeding protocol, bioreactor and cultivation conditions, which will influence the structural and functional characteristics of the final tissue-engineered construct, should be selected to provide an ideal environment for in vitro tissue growth. For example, in the case of a cardiac tissue construct, the in vitro system of choice needs to provide an oxygen supply to the cells at all times during cell seeding and construct cultivation.

To this end, polymer scaffolds for cardiac tissue engineering have been seeded using a variety of techniques. For example, concentrated cell suspensions have been added to scaffolds (R. K. Li et al., Circulation, 1999, 100: II63-II69; R. K. Li et al., J. Thorac Cardiovasc. Surg. 2000, 119: 368-375). Suspensions of cardiomyocytes have also been seeded onto substrates in orbitally mixed dishes (R. L. Carrier et al., Biotechnol. Bioeng. 1999, 64: 580-589), in spinner flasks (N. Bursac et al., Am. J. Physiol. 1999, 277: H433-H444; R. L. Carrier et al., Biotechnol. Bioeng. 1999, 64: 580-589), and in rotating vessels (M. Papadaki et al., Am. J. Physiol: Heart Circ. Physiol. 2001, 280: H168-H178).

Although all these methods resulted in constructs with viable cells, the cell distribution was highly inhomogeneous. Cardiac constructs cultured in well-mixed medium had an approximately 100 μm-thick peripheral tissue-like region around a relatively cell-free interior, a structure consistent with the presence of concentration gradients within the tissue. This is most likely due to the fact that, in these systems, the oxygen dissolved in the medium is transported to the cells by molecular diffusion, which provides enough oxygen for a thin outer layer of functional tissue but not to the construct interior, which remains relatively acellular (N. Bursac et al., Am. J. Physiol. 1999, 277: H433-H444; R. L . Carrier et al., Biotechnol. Bioeng. 1999, 64: 580-589; M. Papadaki et al., Am. J. Physiol: Heart Circ. Physiol. 2001, 280: H168-H178; W. H. Zimmermann et al., Biotechnol. Bioeng. 2000, 68: 106-114).

Thus, whereas human heart muscle is up to 2 centimeters thick, growth of bioartificial tissue equivalents in bioreactors typically stops once the construct is about 100 μm thick, i.e., about 4 to 7 cell layers thick. Beyond this thickness, the innermost cells are too far from the supply of fresh growth medium to thrive. The formation of 1 to 5 mm thick, functional constructs based on cells that cannot tolerate hypoxia for prolonged periods of time (for example, cardiac myocytes) depends on the ability to seed the cells at a high and spatially uniform initial density as well as on the capacity to maintain their viability and function. Therefore, in order to engineer tissue constructs with a certain threshold thickness, uniformity of tissue architecture and functionality, it is necessary to overcome oxygen diffusional limitations during both the steps of scaffold seeding and of construct cultivation. In one embodiment, scaffolds are 1.5 mm thick (dry thickness) or greater, for example, at least 2 mm, at least 3 mm, or at least 4 mm thick.

In order to enhance mass transport between culture medium and cells within cultured constructs, perfused bioreactor systems have been developed (R. L. Carrier et al., Biotechnol. Bioeng. 2002, 78: 617-625; R. L. Carrier et al., Tissue Eng. 2002, 8: 175-188). In these systems, cells are seeded onto a scaffold in tissue culture dishes for 2 to 3 days and subsequently cultured for about 1 week in a bioreactor that forces the nutrient medium to perfuse directly through the cell-seeded construct instead of simply flowing around it. The transport of oxygen from the medium to the cells occurs via diffusion during cell seeding and by a combination of diffusion and convection during cultivation, which better mimics the transport conditions within native tissue. Furthermore, during cultivation, the flow of medium redistributes the cells evenly across the entire volume of the construct, leading to homogenous spatial organization of the cells. However, in the tissue constructs obtained using these methods, the cell density remained low due to the limitations in oxygen transport during the cell seeding step.

A new seeding/cultivation strategy which combines the methods for rapid gel inoculation (G. A. Ameer et al., J. Orthop. Res. 2002, 20: 16-19) and direct medium perfusion through the seeded scaffold (S. S. Kim et al., Tissue Eng. 2000, 6: 39-44) has recently been developed in the applicant's laboratory and found to result in high rate, yield, viability and uniformity of cell seeding (M. Radisic et al., Biotechnol. Bioeng. 2003, 82: 403-414). In these studies, cells (neonatal rat cardiomyocytes) were seeded at initial densities comparable to those found in adult rat myocardium (i.e., ~$10^8$ cells/$cm^3$; C. A. Mandarim-de-Lacerda and L. M. M. Pereira, Pathobiology, 2000, 68: 36-42) into a collagen sponge (13 mm×3 mm discs), using Matrigel® as a vehicle for rapid cell delivery. Scaffolds inoculated with cell-gel suspension were then seeded in perfused cartridges with alternating medium flow. Medium perfusion through the cell-polymer construct was established immediately in order to maintain the viability of inoculated cells during cell attachment to substrates and subsequent construct cultivation. This strategy produced thick, compact and functional cardiac muscle tissue with more evenly distributed cells and much higher cell densities than any previous study.

Figure 1A:
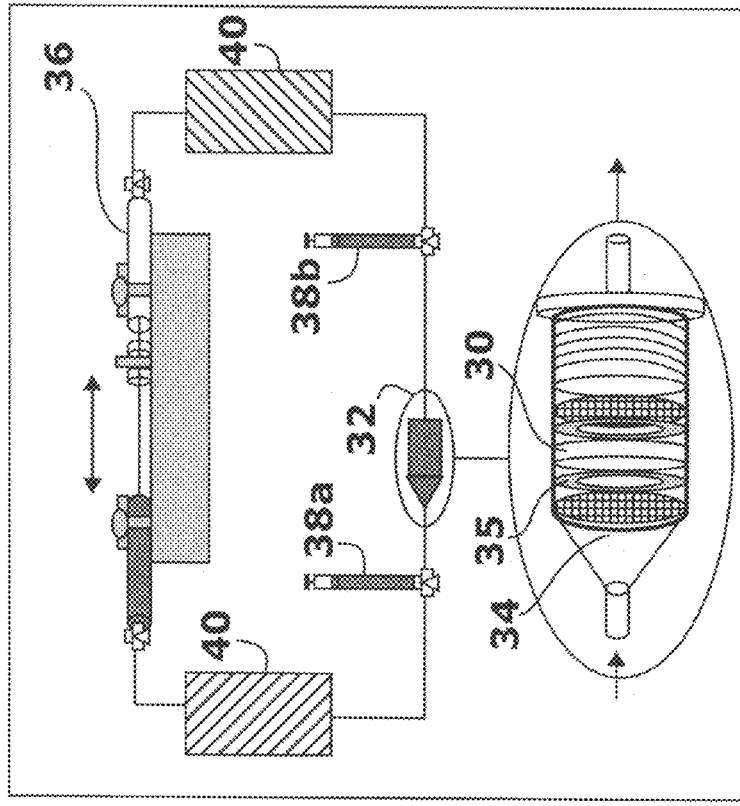
FIG. 1A is a schematic diagram of an exemplary perfusion system for seeding of some constructs according to an embodiment of the invention.

In an exemplary perfusion system, a construct 30 is disposed in a cartridge 32 between two stainless steel support screens 34 (FIG. 1A). Silicone gaskets 35 protect the construct 30 from the steel screens 34. The cartridge 32 is connected to a push/pull syringe pump 36. Each side of pump 36 is connected to de-bubbling syringe 38 to remove air bubbles. Gas exchangers 40 allow regulation of the gasses dissolved in culture media circulated through the system.

In all the methods described above, the cell-seeded construct is cultivated in a nutritive medium. Nutritive media for mammalian cell cultures are well known in the art. Generally, culture media contain essential nutrients, trace elements, vitamins, lipids, electrolytes, and sources of energy. Other additives include serum from fetal, new born or adult cows, growth factors, cytokines, and functional modulators. The choice of the culture medium and of its components, which affect the proliferation, growth, and function of cells and alter cell phenotype in culture, will depend on the mammalian cells used in the preparative methods. Media for the culture of mammalian cardiac cells are known in the art (see, for example, S. N. Mohamed et al., In Vitro Cell and Develop. Biol. 1983. 19: 471-478; P. Libby, J. Mol. Cell. Cardiol. 1984. 16: 803-811; D. L. Freerksen et al., J. Cell. Physiol., 1984, 120: 126-134; G. Kessler-Icekson et al., Exp. Cell Res. 1984. 155: 113-120; J. S. Karliner et al., Biochem. Biophys. Res. Comm. 1985. 128: 376-382; T. Suzuki et al., FEBS Letters, 1990, 268: 149-151; T. Suzuki et al., J. Cardiov. Pharmacol. 1991, 17: S182-S186; T. Suzuki et al., J. Mol. Cell. Cardiol. 1997, 29: 2087-2093). Different factors and agents may be added to the culture medium. In certain embodiments, the in vitro cultivation of the cell-seeded construct is carried out under conditions selected to promote deposition of extracellular matrix components. The in vitro cultivation of the cell-seeded construct may also be carried out under conditions that promote cell proliferation and/or cell differentiation.

The cultivation dish or bioreactor is placed into an incubator, which provides a controlled environment. The temperature of the incubator is generally set at 37° C., and the relative humidity of the incubator is held at 90%. The composition of the gas environment in the incubator depends on the selection of the medium. For example, a mixture of air with 5% $CO_2$ may be used in combination with a bicarbonate-buffered medium, while air alone may be used when a HEPES-buffered medium is utilized.

Tissue engineering methods often lead to bioartificial tissue constructs, that, unlike native cardiac tissue, which consists of parallel fibers with defined orientation, contain cells that exhibit random orientation and a poor degree of differentiation. In order to achieve a more tissue-like organization of the cells on the substrate, the inventive methods include physiological electrical stimuli during in vitro culture that are thought to be necessary for proper development and differentiation of native and engineered cardiac muscle.

More specifically, the preparative methods of the invention may include cultivating the cell-seeded construct in the presence of a biomimetic electrical stimulation. Specific conditions of electrical stimulation (nature, amplitude, frequency) are designed to mimic the electrical stimulation received by a specific native tissue in vivo. For example, cardiac tissue constructs of the invention are preferably cultivated in the presence of an electrical stimulation that mimics the electrical stimulation received by a cardiac muscle tissue in vivo.

In certain embodiments, the electrical stimulation is used to differentiate cardiac progenitor cells and/or stem cells into cardiac myocytes. Results from experiments carried out by the applicants suggest that when cardiac-like electrical stimulation is applied during in vitro cultivation, there is no need for chemical factors (such as, for example, 5-azacytidine) to induce cell differentiation. Therefore, cardiac-like electrical stimulation of human mesenchymal stem cells can be used to generate cardiac-like cell phenotype without the application of any specific chemical factors.

As illustrated in the Examples below, the inventive methods lead to the formation of cardiac muscle constructs with improved structural and functional characteristics. In particular, cardiac constructs cultivated in the presence of a biomimetic electrical stimulation were found to exhibit aligned nuclei and thick aligned myofibers expressing cardiac troponin I and sarcomeric α-actin, while constructs cultured in the absence of electrical stimulation (all other conditions being the same) consisted of mostly round, mononucleated cells with lower level of differentiation.

The inventive preparation methods may be applied to produce bioartificial equivalents of other native tissues that contain electrically excitable cells and are subject to electrical stimulation in vivo. Thus, the electrical stimulation used to form these tissue-engineered constructs may be chosen to mimic the electrical stimulation received by a striated skeletal muscle tissue, smooth muscle tissue, bone, vasculature, or nerve tissue in vivo.

Characteristics of electrical stimulations received by native tissues in vivo are known in the art. The electrical stimulation may be generated by any suitable system. For example, commercially available cardiac stimulators, which can produce electrical stimuli that mimic the electrical stimuli received by native cardiac tissues in vivo, may be used in the preparation of cardiac constructs. Other methods include using impulse generators in custom-made electric circuits.

The progress of the formation of a tissue-engineered construct may be assessed using different methods. For example, in the case of a cardiac muscle tissue construct, the spontaneous or stimulated contractile activity of the cultivated construct may be determined non-invasively. Properties such as strength, elasticity, conductivity, tissue organization, cellular organization, cell viability, cell morphology, metabolic activity, cell cycle propagation, ultrastructural features, electrical signal propagation, gene expression and protein expression may be studied on small pieces of the cultivated construct. Alternatively or additionally, samples of the culture medium may be analyzed for the presence of metabolites and waste products.

Once the culture has progressed enough that the cells exhibit the three-dimensional cellular organization of the desired tissue over a significant portion of the substrate, cultivation of the construct may be stopped. Adequate incubation times and parameters which depend on the cells, medium and support used in the construct preparation can easily be determined by one skilled in the art.

In addition to involving an electrical stimulation, the methods of preparation of the invention may further include the step of stimulating the cell-seeding construct mechanically and/or chemically. For example, Eschenhagen and coworkers have submitted cardiac patches formed using cardiac muscle cells from newborn rats to stretching (C. Fink et al., FASEB J. 2000, 14: 669-679), and have shown that when these engineered tissues are implanted into rats, they contracted up to four times more vigorously than unstretched tissues (T. Eschenghagen et al., Transplant Immunol. 2002, 9: 315-321). Other examples of mechanical stimulation include strain, hydrostatic pressure, direct compression, "high-shear fluid environments", and "low-shear fluid environments". Multi-directional mechanical stimulation may also be used. For example, a construct may be strained in one direction at its comers and in a different direction in the center. In addition, the mechanical stimulation may be constant or intermittent. For example, a pulsed mechanical stimulus to imitate the contraction of heart muscle or of the flow of blood may be applied.

Chemical stimulation is often used during cultivation of tissue engineering constructs to induce cell differentiation. For example, marrow stromal cells have been shown to spontaneously start beating after exposure to 5-azacytidine, a cytosine analog capable of altering expression of certain genes that may regulate differentiation (S. Makino et al., J. Clinical Invest. 1999, 103: 697-705). Similarly, agents used to induce neural differentiation from bone marrow or umbilical cord blood include retinoic acid, β-mercaptoethanol, antioxidants, demethylating agents, compounds that increase intracellular cyclic AMP (e.g., isobutylmethylxanthine), and physiological neural inducers (e.g, noggin) (J. R. Sanchez-Ramos, J. Neuroscience Res. 2002, 69: 880-893).

In other embodiments, the inventive preparative methods further include the step of treating the three-dimensional tissue-engineered construct with at least one biologically active agent. The biologically active agent may include one or more of growth factors, adhesion factors, soluble extracellular matrix proteins, antibiotics, agents that enhance vascularization, agents that enhance cell differentiation, agents that enhance tissue differentiation, agents that inhibit fibrosis, agents that inhibit tumorigenesis, agents that enhance cell proliferation, agents that inhibit cell proliferation, agents that inhibit scaffold degradation, agents that enhance scaffold degradation, agents that enhance histocompatibility, and agents that enhance hemocompatibility. Exemplary biologically active agents that may be exploited for use with the invention include but are not limited to activin A (ACT), retinoic acid (RA), epidermal growth factor, bone morphogenetic protein, platelet derived growth factor, hepatocyte growth factor, insulin-like growth factors (IGF) I and II, hematopoietic growth factors, peptide growth factors, erythropoietin, interleukins, tumor necrosis factors, interferons, colony stimulating factors, heparin binding growth factor (HBGF), alpha or beta transforming growth factor (α- or β-TGF), fibroblastic growth factors, epidermal growth factor (EGF), vascular endothelium growth (VEGF), nerve growth factor (NGF), muscle morphogenic factor (MMP), integrins, and amino acid sequences including cell binding regions such as RGD).

The choice of the specific cultivation conditions will depend on the nature of the construct desired as well as on the intended purpose of the final tissue engineered product. In certain embodiments, after preparation, the construct is stored before being used. In other embodiments, the construct is used immediately after preparation.

II. Three-Dimensional Tissue-Engineered Constructs

In an exemplary embodiment, the present invention is directed to three-dimensional tissue-engineered constructs including mammalian cells organized on a substrate to provide a three-dimensional cell structure having structural and functional characteristics of a native tissue. Preferably, the three-dimensional cell structure is obtained by contacting the substrate with mammalian cells to form a cell-seeded construct, and cultivating the resulting construct in vitro in the presence of a biomimetic electrical stimulation.

Suitable substrates and cells as well as cultivation conditions for these, are as described above. When the construct is a cardiac muscle construct, the cells may include one or more of cardiomyocytes, endocardial cells, cardiac adrenergic cells, cardiac fibroblasts, vascular endothelial cells, smooth muscle cells, cardiac progenitor cells, and stem cells. During the cultivation period, the cell-seeded construct is submitted to an electrical stimulation that mimics the electrical stimulation received by a cardiac muscle tissue in vivo. Inventive cardiac constructs may have different shapes depending on their intended use. For example, they may be grown as pieces of tissue to be used as patches, or they may be grown to resemble heart valves.

III. Therapeutic Uses of Inventive Constructs

In another aspect, the present invention provides methods for treating an individual suffering from tissue deficiency, damage or loss. These methods may include producing a three-dimensional tissue-engineered construct according to the methods of preparation described above, implanting the construct into the individual in need thereof, and submitting the implanted construct to a biomimetic electrical stimulation. The inventive methods of treatment are particularly useful when the native tissue to be replaced or supplemented is one which contains electrically excitable cells and is subject to electrical stimulation in vivo. Examples of such tissues include, but are not limited to, cardiac muscle tissue, striated skeletal muscle tissue, smooth muscle tissue, bone, vasculature, and nerve tissue.

The electrical stimulation applied to the construct in vivo following implantation may have several functions. It may enhance the integration of the engineered construct with host tissue and allow the formation of a direct structural and functional connection between the implanted engineered construct and the native host tissue. Additional or alternatively, the electrical stimulation may increase cell survival and/or cell functionality in vivo.

In some embodiments, it may be desirable to prepare the construct and implant it without having first exposed the construct to a biomimetic electrical stimulation. Instead, the construct is subjected to such stimulation after implantation. The construct is provided with a synthetic or natural lead to connect it to a source of electrical stimulation. For example, nervous tissue from elsewhere in the native tissue may be joined to the construct using standard surgical techniques. A pacemaker may be implanted and connected to the construct, or the patient may carry an external power source connected to the implanted construct.

In certain embodiments, the inventive methods are used for treating an individual suffering from tissue deficiency, damage or loss that is associated with an acute or chronic heart condition. Medical indications for such a treatment include coronary heart disease, cardiomyopathy, endocarditis, congenital cardiovascular defects, and congestive heart failure. A final common pathway of many cardiovascular diseases is irreversible damage of the cardiac muscle tissue. This effect is generally attributed to the inability (or weak capacity) of cardiac cells to replicate after injury (M. H. Soonpaa and L. D. Field, Circ. Res. 1998, 83: 15-26) as well as to the lack of a substantial source of resident stem cells in the myocardium.

Excessive loss of cardiomyocytes due to ischemia (deficiency of blood flow) and formation of scar tissue are, for example, observed after myocardial infarction. Myocardial infarction is a leading cause of heart failure and death in developed countries. According to the American Heart Association, in 2000, approximately 1.1 million Americans suffered from a myocardial infarction, usually as a result of a heart attack. Infarcts occur when a coronary artery becomes obstructed and no longer supplies blood to the myocardial tissue. The damage of myocardial infarction is generally progressive (D. L. Mann, Circulation, 1999, 100: 999-1008). However, the consequences are often severe and disabling. Immediate hemodynamic effects are followed by three major processes: infarct expansion, infarct extension, and ventricular remodeling. The magnitude and clinical significance of these processes highly depend on the size and location of the myocardial infarction (H. F. Weisman and B. Healy, Prog. Cardiovasc. Dis. 1987, 30: 73-110; S. T. Kelley et al., Circulation, 1999, 99: 135-142).

Early after a myocardial infarction, infarct expansion takes place through slippage of the tissue layers, which results in a permanent regional thinning and dilation of the infract zone. Infarct extension corresponds to additional myocardial necrosis and produces an increase in total mass of infarcted tissue. The presence of infarcted tissue (i.e., scar tissue that is unable to contract during systole) leads to a depression in ventricular function, and eventually to dysfunction in cardiac tissue remote from the site of initial infarction. This greatly exacerbates the nature of the disease and can often progress into advanced stages of congestive heart failure. The third process, ventricular remodeling, usually happens weeks or years after myocardial infarction. It corresponds to a progressive enlargement of the ventricle with depression of ventricular function, and is believed to result from the high stress undergone by tissues surrounding the initial infarction zone (D. K. Bogen et al., Circulation Res. 1980, 47: 728-741; J. Lessick et al., Circulation, 1991, 84: 1072-1086). Deterioration of the ventricular function eventually leads to heart failure (D. L. Mann, Circulation, 1999, 100: 999-1008).

Despite recent advances in the treatment of acute myocardial infarction, the ability to repair extensive myocardial damage and to treat heart failure is limited (D. L. Mann, Circulation, 1999, 100: 999-1008). A possible strategy to restore heart function after myocardial injury is to replace the damaged tissue with healthy tissue. Experiments have shown that the strategy of tissue engineering could be used for regeneration and healing of the infarcted myocardium and attenuation of wall stress, infarct expansion and left ventricle dilatation. These beneficial effects could be translated into the prevention of heart failure progression (J. Leor et al., Circulation, 2000, 102: III56-III61).

Inventive cardiac muscle constructs may be implanted into patients after myocardial infarction to provide for augmentation of cardiac tissue and contractile function. After implantation, such tissue-engineered constructs will act as ventricular "patch" of functional cardiac tissue or "contracting living Band-Aid". One, or more than one, cardiac construct may be implanted into, for example, infarcted area(s) of the heart to help re-establish the correct propagation of the contractile signal and to provide contractile elements.

Inventive constructs in the shape of heart valves may find applications as blood vessel substitutes in heart bypass surgery. More than 500,000 coronary artery bypass operations are performed annually in the U.S. alone. Bypass surgery may be needed for various reasons, for example, to restore blood flow to cardiac tissue that has been deprived of blood because of a coronary artery disease, or in the case of an angioplasty that did not sufficiently widen the blood vessel, or because of blockages that cannot be reached by, or are too long or stiff for, angioplasty. In conventional coronary artery bypass graft operation, a piece of vein taken from the leg of the patient, or from an artery from the chest or wrist is attached to the heart artery above and below the narrowed area, thus making a bypass around the blockage.

These procedures substantially improve symptoms in more than 90% of patients who undergo the treatment. A graft may be placed to any one of the following arteries: left main coronary artery, which supplies the left ventricle of the heart; the left anterior descending artery; obtuse marginal branch of the circumflex artery; circumflex artery; right coronary artery; and posterior descending artery. Better results are obtained if one of the patient's own vessels is grafted. If an autologous vessel cannot be used, a prosthetic vessel may be implanted. However, synthetic grafts that are foreign to the body may pose long-term health risks. Furthermore, synthetic materials are not useful for the construction of the small diameter grafts that are required for many heart bypass surgeries, as the grafts are more prone to clotting.

Therefore, inventive constructs in the shape of heart vessels, especially those prepared using autologous cells, appear as a potential alternative with several advantageous properties, such as avoidance of anti-coagulant therapy, a potential for growth as well as greater durability and longevity.

Other medical indications for the inventive methods of treatment include congenital heart defects. When the heart or blood vessels near the heart do not develop normally before birth, a condition called congenital defect occurs. Most heart defects cause an abnormal blood flow through the heart or obstruct blood flow in the heart and vessels. Congenital heart defects include obstruction defects (such as aortic stenosis, pulmonary stenosis, bicuspid aortic valve, subaortic stenosis and coarctation of the aorta), septal defects (such as atrial septal defect, Ebstein's anomaly and ventricular septal defect), cyanotic defects (such as tetraology of Fallot, tricuspid atresia and transposition of the great arteries), hypoplastic left heart syndrome and patent ductus arteriosus.

Depending on the specific heart defect experienced by the patient, an inventive cardiac muscle patch or engineered heart valve can be implanted to correct the heart's deficiency.

Efficacy of these treatments can be monitored by clinically accepted criteria, such as reduction in area occupied by scar tissue or revascularization of scar tissue, and/or in an improvement in developed pressure, systolic pressure, end diastolic pressure, patient mobility and quality of life.

To determine the suitability of the methods of treatment provided by the present invention, inventive three-dimensional constructs can first be tested in animal models. Tissue-engineered constructs can, for example, be implanted into immunodeficient animals (such as nude mice or other animals rendered immunodeficient chemically or by irradiation) and the implanted construct(s) may be submitted to a biomimetic electrical stimulation to enhance the integration of the grafted tissue and increase cell survival and functionality in vivo. Heart of small animal models can be cryoinjured by placing a precooled aluminum rod in contact with the surface of the anterior left ventricle wall (C. E. Murry et al., J. Clin. Invest. 1996, 98: 2209-2217; H. Reinecke et al., Circulation, 1999, 100: 193-202; U.S. Pat. No. 6,099,832). In larger animals, cryoinjury can be inflicted by placing a 30-50 mm copper disk probe cooled in liquid nitrogen on the anterior wall of the left ventricle for about 20 minutes (R. C. Chiu et al., Ann. Thorac. Surg. 1995, 60: 12-18). Infarction can be induced by ligation of the left main coronary artery (Q. Li et al., J. Clin. Invest. 1997, 100: 1991-1999).

Cardiac muscle constructs can be implanted within an animal model at the site of injury. Suitability of the treatment may be determined by assessing the degree of cardiac recuperation that follows the implantation. Cardiac function may be monitored by determining such parameters as left ventricular end-diastolic pressure, developed pressure, rate of pressure rise, and rate of pressure decay. After a certain period of implantation, tissues may be harvested and studied by histology. Cells of the tissue harvested may be tested for their ability to survive and maintain their phenotype in vivo. The presence and phenotype of the cells can be assessed by immunohistochemistry or ELISA using specific antibody, or by RT-PCR analysis.

Other types of constructs such as bioartificial equivalents of striated skeletal muscle tissue, smooth muscle tissue, bone, vasculature, or nerve tissue produced by the preparative methods of the invention may also be used in a large range of clinical applications.

For example, nerve injuries have a significant impact on the quality of life. In the United States, an estimated 235,000 individuals suffer from physically debilitating spinal cord injuries, with total associated costs of more than $350 billion. Peripheral nerve injuries, such as facial paralysis and nerve damage in limbs resulting from accidents, occur even more frequently than spinal cord injury. Peripheral nerve injury can result from mechanical, thermal, chemical, or pathological causes and may lead to loss of muscle function or to sensory loss and phantom sensations. In the treatment of peripheral nerve damage, surgeons use a nerve graft from the patient, but regeneration is often incomplete, and, inevitably some irreversible damage occurs. Additional disadvantages include loss of function at the donor site and the need for multiple surgeries, which increase risk and cost to the patient. Nerve defect or damage may be treated by replacing the damaged tissue with inventive nerve tissue constructs, and submitting the implanted construct to a biomimetic electrical stimulation to enhance its integration with the host tissues and/or to maximize cell survival and/or cell functionality in vivo.

IV. Inventive Constructs as in Vitro Tissue-Equivalents

In addition to their use as advanced bioartificial substitutes for in vivo implantation, or to remodel and regenerate tissue for the purpose of repairing, replacing, maintaining, or enhancing organ function, three-dimensional tissue-engineered constructs also have important in vitro applications. Bioartificial tissue equivalents can be useful, for example, as biosensors, as model systems for fundamental research studies and education, as well as in drug research and development, including for toxicity and pharmacological testing of existing drugs, screening of potential therapeutic candidates, and identification and validation of new targets.

Inventive three-dimensional tissue-engineered constructs with structural and functional characteristics of a native tissue exhibit several advantageous properties over conventional model systems such as animals and cell cultures. Due to differences between species, animal models are not always adequate representations of human biology. This often precludes the extrapolation of observations made in animal studies to the corresponding situation in humans. In addition, the relevance of in vivo controls is often limited due to differences between animals of the same species. Similarly, cell cultures are far from being ideal model systems. Cells placed in culture adopt a two-dimensional monolayer configuration that is different from the organization of cells within a native tissue. This generally leads to a loss of at least some key physiological functions and activities that the cells normally have as part of an organized tissue in the body. It is known that dimensional interactions among various cells, as well as interactions between cells and their external environment, affect physiological functions in a variety of systems (see, for example, M. Marx et al., J. Clin. Invest. 1994, 93: 131-139; E. L. Huguet et al., J. Biol. Chem. 1995, 270: 12851-12856; S. Sankar et al., J. Clin. Invest. 1996, 97: 1436-1446; M. Kitamura et al., Am. J. Physiol. 1996, 270(4 Pt 2): F614-F622). Thus, while cultured cells may be adequate for some applications, for example in drug metabolism and detection of toxins, they fail for others. Bioartificial tissues (especially human tissue equivalents) that are able to mimic the physiological responses of intact organs, therefore appear as more relevant model systems for in vitro research and drug testing.

Accordingly, the present invention provides methods of using the inventive tissue-engineered constructs under in vitro conditions. These methods comprise producing a three-dimensional construct according to the inventive methods of preparation described above; exposing the construct to a test factor; and observing the response of the construct to the test factor.

Exposing the construct to a test factor may include submitting the construct to a mechanical stimulus or to an electrical stimulus. Alternatively, exposing the construct to a test factor may include submitting the construct to an experimental protocol, such as sample preparation by homogenization, fixation, dehydration, sectioning, washing, incubation, staining, immuno-staining, and the like. Exposing the construct to a test factor may include submitting the construct to a certain temperature, pH, gas content or oxygen concentration, or contacting the construct with an inorganic molecule, an organic molecule, a biologically active agent (such as those listed above), a plant extract, a drug or a potential therapeutic candidate.

Observing the response of the construct to the test factor may be done by studying or assessing any property of the construct at the macroscopic (i.e., tissue) and/or at the cellular level; or by evaluating or determining a change in any property of the construct. Exemplary properties of the construct that can be investigated are strength, elasticity, durability, conductivity, contractility, tissue organization, cellular organization, cell viability, cell morphology, metabolic activity, cell cycle progression, fraction of apoptotic cells, ultrastructural features, electrical signal propagation, gene expression, and protein expression.

Depending on the response of the construct to be observed, different methods may be used to assess the property of interest. Such methods are well-known to those skilled in the art. For example, the construct may be attached to at least one strain gauge, and the response of the construct measured as a change in the strain. A dye may also be added to the construct and the response of the construct to the test factor observed using a detection instrument sensitive to the dye. For example, the dye may be selected to reveal the general structure of the construct. Additionally or alternatively, the dye may be selected to specifically stain a specific structural feature or component of the engineered construct in order to reveal the presence or allow the quantification of that particular feature or component. Examples of detection instruments sensitive to dyes include spectrophotometer, spectrofluorometer, confocal laser scanning microscope, and the like.

Particularly interesting is the use of the inventive three-dimensional tissue-engineered constructs as cell culture systems with suitable mimicry for in vitro analysis and testing of drugs and/or screening of potential therapeutic candidates. In addition to offering the advantage of investigating the effects of drugs in the context of the native tissue, the inventive methods of preparation also allow the production of multiple tissue-equivalent materials from a single donor organ, which eliminates, or significantly reduces, the problems of controls and sample differences.

Drugs that are targeted to a specific tissue in the body may be tested using a corresponding inventive tissue equivalent to determine their safety, efficacy and mechanism of action by studying their effects on different properties of the tissue construct. For example, the effects of modulators or potential modulators of contractile activity may be studied using tissue-engineered cardiac muscle tissue. Drugs may be tested for their effects on tissue maintenance and/or repair. It may also be desirable to use bioartificial cardiac muscle tissue to verify the safety and arrhythmogenic potential of drugs that are not targeted to the cardiovascular system but may produce unwanted side effects.

Any change in the properties of the tissue construct (for example, in tissue organization, contractile activity, electrophysiology, cell organization, cell viability, cell survival, cell morphology, metabolic activity, expression of certain markers and receptors, etc.) that is attributable to the drug or potential therapeutic candidate (compared with untreated tissue constructs or tissue constructs treated with an inert compound) is identified. The effect of the drug or therapeutic candidate is then correlated with the observed change.

Studying three-dimensional inventive constructs with structural and functional characteristics of a native tissue can also help expand the understanding of the organ biology. This is particularly true in the case of the heart, which is a difficult and complex organ to investigate. Surgical intervention in a living animal with a defective heart often leads to a shut-down of most of the other critical systems, such as the lungs and kidneys, which is generally followed by death of the animal. Furthermore, cell-cell and cell-matrix interactions are more readily observed in tissue equivalents than in the less controllable, more complex intact organs. Using the inventive preparation methods, the initial proportion and type of cells and matrix constituents in a construct can be independently varied. Although cells secrete extracellular matrix components during tissue development, these are relatively insignificant at early stages and may become more important later. This simplification of tissue composition allows for a more informative characterization of the properties of the cells and matrix in the tissue and in comparison with the same constituents in isolation. Building up the complexity of composition of the tissue can then reveal the functions of the specific constituents added. The flexibility offered by the preparative methods allows the study of cardiac tissue equivalents at different stages of development which could dramatically expand our understanding of cardiac cell biology, cardiac physiology, and the relationships between cardiac function and structure during embryogenesis and cardiac remodeling. In particular, valuable information regarding the differentiation of early human cardiac precursor cells, the development of excitability, excitation-contraction coupling, and the molecular signals involved in these processes could be obtained.

EXAMPLES

The following examples describe modes of making and practicing the present invention. However, it should be understood that these examples are for illustrative purposes only and are not meant to limit the scope of the invention.

In particular, the following examples illustrate the preparation of cardiac muscle tissue using the inventive methods (Example 1), and describe various analytical experiments (Examples 2 to 9) that can be carried out (a) to demonstrate the cardiac-specific features of the constructs produced, (b) to evaluate construct structure, and (c) to assess their electrophysiological and contractile properties on a macroscopic (i.e., tissue) level as well as on a cellular level. Example 10 describes a method of cardiac differentiation of embryonic stem cells by electrical stimulation. Example 11 describes an exemplary method of cultivating cell-seeded constructs in perfusion. Example 12 describes an exemplary method of applying the techniques of the invention to mesenchymal stem cells.

Example 1

Preparation of Bioartificial Cardiac Muscle Tissue

Cardiac Myocyte Preparation. Primary cultures of cardiac myocytes were prepared by enzymatic digestion of ventricles obtained from neonatal (2 day old) Sprague-Dawley rats (Taconic), as previously described (M. Toraason et al., Toxicology, 1989, 56: 107-113, the contents of which are incorporated herein by reference). Briefly, ventricles (n=50, 5 litters in 3 independent studies) were incubated with 0.1% trypsin overnight and dissociated in four to five sequential steps using 0.1% collagenase.

Cell-Seeded Construct Preparation. Isolated cardiac myocytes were suspended in Matrigel® ($10^6$ cells/5 μL) and seeded onto Ultrafoam™ collagen sponge scaffold (6×8×1.5 mm) at the density of $0.8 \times 10^8$ cells/cm$^3$.

Figure 2:
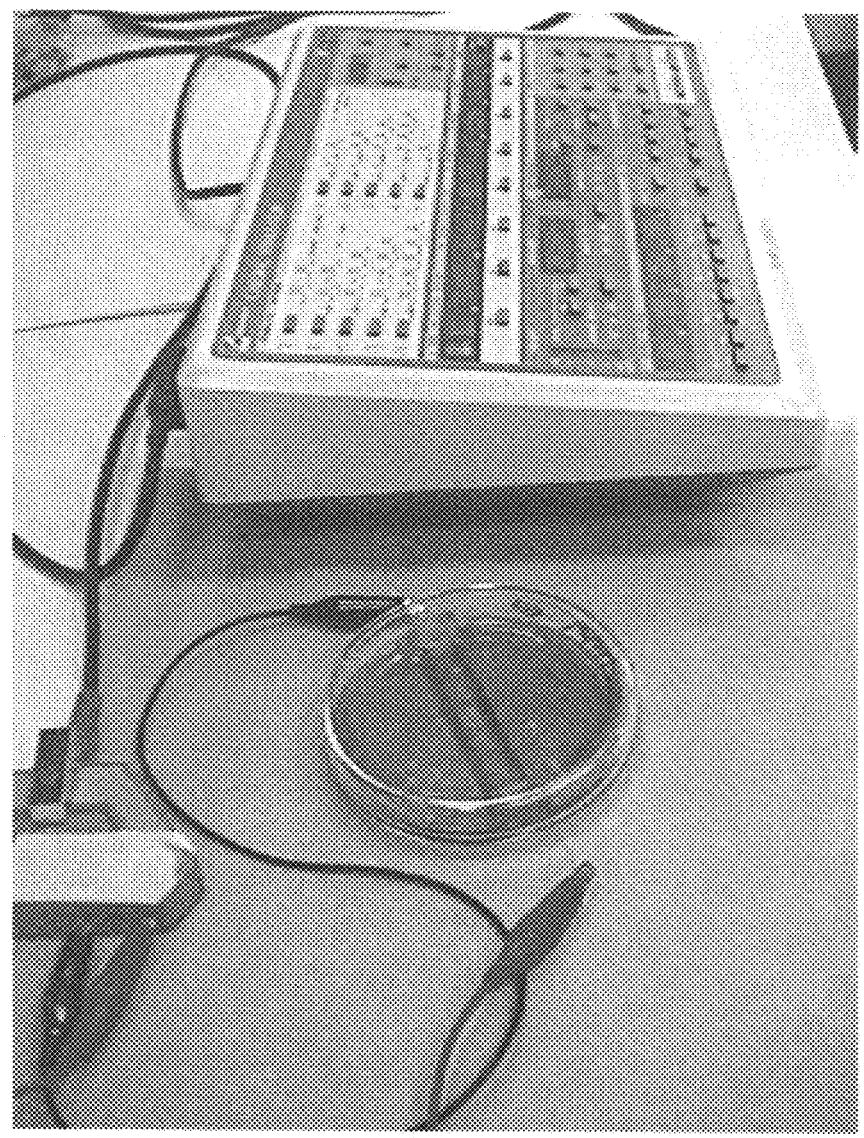
FIG. 2 is a photograph showing a multi-well simulation chamber having two carbon electrodes that are connected to a commercial cardiac stimulator via two platinum wire and alligator clamps.
Figure 3A:
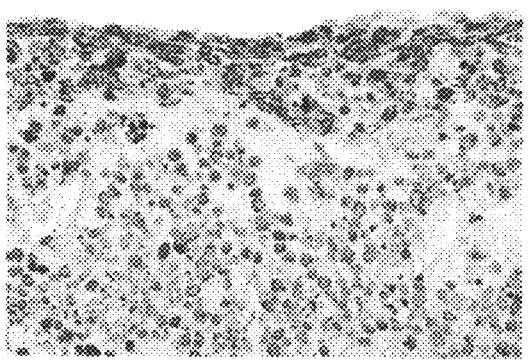
FIG. 3 is composed of 4 fluorescence microscope images of stained cardiac constructs cultivated in the presence and in the absence of an electrical stimulation. The alignment of myotubes and expression of contractile proteins in engineered cardiac tissue cultivated for 8 days in a standard set-up are displayed in parts A and B, while parts C and D present the same features for a cardiac muscle tissue cultivated in one particular series of experiments for a total period of 8 days (including 5 days of cultivation in the presence of an electrical stimulation). Parts A and C show staining of the contractile protein cardiac troponin I. Parts B and D show staining of the contractile protein sarcomeric α-actin (see Example 2 for a description of the experimental conditions used to stain the contractile proteins).
Figure 3B:
Figure 3C:
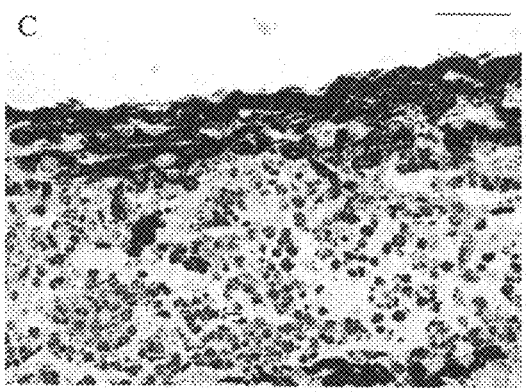
Figure 3D:
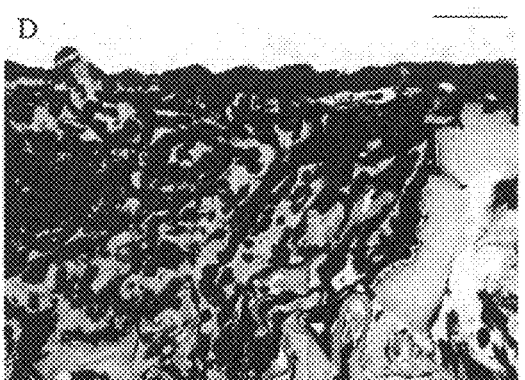

Cultivation of Cell-Seeded Construct. After 3 days of cultivation, the engineered tissue was transferred to a chamber consisting of a 100 mm glass Petri dish fitted with two ¼" diameter carbon rods (stimulating electrodes) connected to a commercial cardiac stimulator (Nihon Kohden) via platinum wires (as presented in FIG. 2). Silicone tubing spacers were used to create six wells between the two electrodes, enabling the cultivation of six constructs per Petri dish. Engineered tissue was stimulated with square pulses, 2 ms duration, at 60 beats per minute (bpm) and 5 V for 5 days. The stimulation voltage was adjusted to be the minimal required to induce synchronous contractions (observable with optical microscope at 10× magnification) of the engineered tissue. Engineered tissue placed in an identical chamber but without electrical stimulation served as control. All chambers were orbitally mixed at 25 rpm. All experiments were performed in a 37° C./5% $CO_2$ humidified incubator. The culture medium was Dulbecco's Modified Eagle Medium (DMEM) containing 4.5 g/L of glucose supplemented with 10% Fetal Bovine Serum, 10 mM HEPES, 2 mM L-glutamine and 100 units/mL penicillin.

In the following examples, heart ventricles were used for comparison purposes whenever necessary. Heart ventricles were obtained from 2-day old rats following decapitation. For biochemical and histological assessments, small pieces of the ventricles (7-13 mg wet wt) were used. For electrophysiological studies, full-thickness pieces of the ventricular wall (~6×4 mm$^2$, 1.5-2.5 mm thick) were prepared by bisecting heart ventricles. The properties of the ventricles were compared with those of the inventive cardiac muscle constructs without a priori assumption that the engineered product resembled the native ventricular tissues.

Example 2

Histological and Immunohistochemical Assessments

General Evaluation. Cardiac muscle constructs obtained as described in Example 1 in the presence or in the absence of electrical stimulation were rinsed in PBS, and immersed in 10% neutral buffered formalin (Sigma-Aldrich). Samples were embedded in paraffin, sectioned at 5 μm, and stained with hematoxylin and eosin (H+E) for general evaluation.

Tissue Architecture and Cell Distribution. Staining for cardiac troponin I, sarcomeric α-actin, α-myosin heavy chain (α-MHC), β-myosin heavy chain (β-MHC) (myocyte-specific contractile proteins) and connexin-43 (Cx-43, gap junctional protein) was used to assess the fraction and distribution of cardiac myocytes in the constructs.

For immunohistochemical staining, cardiac tissue sections were depariffinized and antigen was retrieved by heat treatment for 20 minutes at 95° C. in decloaking chamber (Biocare Medical). Subsequently, endogenous peroxidase activity was quenched by incubation in 0.3% hydrogen peroxide for 30 minutes at room temperature (RT), the sections were then blocked with 10% horse serum for 30 minutes at RT, then incubated for 1 hour at 37° C. with mouse anti-cardiac troponin I (Biodesign) and mouse anti-sarcomeric α-actin monoclonal (Sigma) antibodies diluted 1:150 and 1:500, respectively in PBS containing 0.5% Tween 20 and 1.5% horse serum. Subsequently, sections were incubated for 30 minutes at RT with a secondary antibody (horse anti-mouse IgG, Standard Elite ABS lit, Vector Laboratories), diluted 1:200, and then with an avidin-biotin complex agent for 30 minutes at RT and 3,3'-diaminobenzidine (Sigma) for 15 minutes at RT. A humidified chamber was used for all incubation steps. Sections were counterstained with Harris hemotoxylin (Sigma-Aldrich) and coverslipped using xylene-based mounting media (Cytoseal). Neonatal rat heart and bovine tendon served as positive and negative controls, respectively. Construct architecture was assessed from stained tissue sections using videomicroscopy and Scion Image software.

For immunofluorescence, sections were depariffinized and antigen was retrieved by heat treatment for 20 minutes at 95° C. in decloaking chamber (Biocare Medical), blocked with 10% horse serum for 40 minutes at RT, then incubated for 1 hour at 37° C. with primary antibodies: mouse anti-α-myosin heavy chain (hybridoma supernatant, ATCC, full strength), mouse anti-β-myosin heavy chain (Chemicon, full strength) and rabbit anti-Connexin-43 (Chemicon, 1:50) diluted in PBS containing 0.5% Tween 20 and 1.5% horse serum. Subsequently, the constructs were incubated with the following secondary antibodies (all from Vector Laboratories) for 30 minutes at 37° C.: Texas Red conjugated horse anti-mouse IgG (1:100) for α-MHC visualization, fluorescein conjugated anti-mouse IgG (1:100) for β-MHC visualization, and fluorescein conjugated goat anti-rabbit IgG (1:200) for Cx-43 visualization. The sections were counterstained with DAPI and coverslipped (Vectorshield mounting medium with DAPI). Neonatal rat ventricles and bovine articulate cartilage served as positive control and negative control, respectively. Construct architecture and cell distribution were assessed from stained tissue sections using a fluorescent microscope (Axioplan, Zeiss) and Open Lab software.

Constructs cultivated in the presence of electrical stimulation exhibited aligned nuclei and thick aligned myofibers expressing cardiac troponin I and sarcomeric α-actin. In contrast, non-electrically stimulated constructs mostly contained round, mononucleated cells with lower level of differentiation (see FIG. 3). Due to the cultivation in an orbitally mixed dish, both groups had cells confined to the ~200 μm thick surface layer.

Cardiac Gap Junctions Assessment. Cardiac gap junctions are membrane specializations that permit the passage of ions and small signaling molecules between myocytes, thus facilitating electrical conduction and chemical communications (E. Page and C. K. Manjunath, *The Heart and the Cardiovascular System*, H. Fozzard et al. (Eds.), Raven: N.Y., 1986, pp. 573-600). The size and spatial distribution of myocyte gap junctions changes during development from a punctuate distribution over the entire cell membrane in neonates to a confined distribution at end-to-end cell connections in adults (R. H. Hoyt et al., Circ. Res. 1989, 64: 563-574; M. J. A. Van Kempen et al., Cardiovasc. Res. 1996, 32: 2195-2200). Gap junctions may be assessed by immunostaining Cx43, a gap junction protein.

Example 3

Biochemical and Molecular Assays

DNA and Protein Assays. Samples for DNA, total protein, and Western blot analyses are homogenized in buffer (1 M $NH_4OH$/2% Triton X-100, 0.04 mL/mg wet wt of sample) for 1 minute. DNA is measured fluorimetrically by Hoescht binding, and total protein is measured by a commercially available kit (Bio-Rad) as previously described (N. Bursac et al., Am. J. Physiol. Heart Circ. Physiol. 1999, 277: H433-H444; R. L. Carrier et al., Biotechnol. Bioeng. 1999, 64: 580-589).

Protein Analysis. The protein expression levels of creatine kinase-MM (CK-MM) and myosin heavy chain (MHC), troponin I and connexin-43 in constructs are quantified as markers of cellular differentiation. Creatine kinase, a dimer of M- or B-type subunits, plays a vital role in the maintenance of cytosolic ATP (L. H. Opie, *The Heart Physiology from Cell to Circulation*, L. Opie (Ed.), Lippincott-Raven: Philadelphia, 1998, pp. 295-342), whereas MHC is involved in the generation of contractile force (L. H. Opie, *The Heart Physiology from Cell to Circulation*, L. Opie (Ed.), Lippincott-Raven: Philadelphia, 1998, pp. 295-342). During cardiac tissue development and differentiation, the muscle-specific CK-MM isoenzyme (J. S. Ingwall, Biochem. Soc. Trans. 1991, 19: 1006-1010; H. Ueno et al., J. Cell Biol. 1988, 107: 1911-1918) and the contractile protein MHC (B. Goldman et al., Exp. Cell Res. 1996, 228: 237-245) are significantly upregulated. The phosphorylation state of Cx43 (determined by collapsing of the 43-kDa band into a 41-kDa band after alkaline phosphatase treatment), is an indication that the gap junctions that are formed during construct cultivation are functional (A. P. Moreno et al., Circ. Res. 1994, 74: 1050-1057).

To quantify the relative expression levels of Cx43, MHC, and CK-MM, the constructs are frozen in liquid nitrogen immediately after the end of the cultivation. Proteins are extracted using ammonium hydroxide extraction buffer (containing 1 M $NH_4OH$, 0.2% Triton X-100) from the scaffolds by steel-ball bead beater. After centrifugation for 10 minutes at 12,000 g at 4° C., the homogenates are stored at −80° C. for further analysis. On the day of the analysis, homogenates are diluted (1 part sample to 2 parts buffer) in Laemni buffer (Bio-Rad) containing 5% mercaptoethanol and 2% SDS and boiled for 5 minutes to denature proteins. Homogenates containing 20 μg of total protein each are separated on 12% Tris-glycine minigels (Bio-Rad) using kaleidoscope prestained standards (Bio-Rad) at a constant voltage of 100 V for 2 hours at room temperature. Three independent constructs from each group are analyzed to compare the expression of the protein bands, and each lane is loaded with the same protein concentration (20 μg).

Figures 4A, 4B:
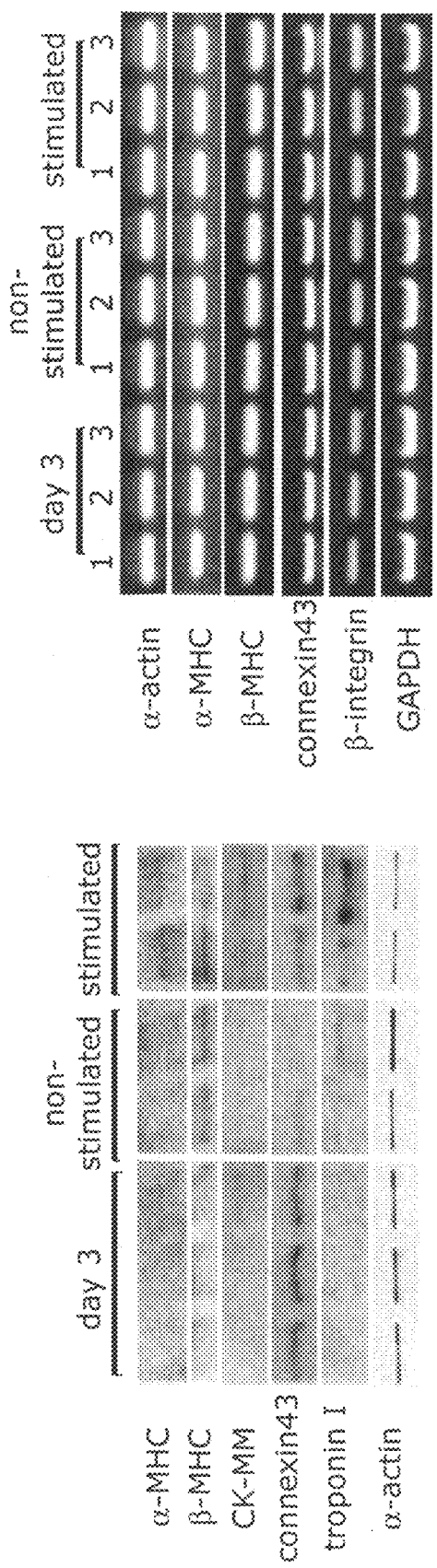
FIG. 4A is a photograph of a set of protein blots for quantitative measurement of protein expression in a construct produced according to an embodiment of the invention. The ratio of alpha MHC to beta MHC is 1.5 after 3 days, 1.4 after four more days in culture without electrical stimulation, and 1.8 after four more days in culture with electrical stimulation.
FIG. 4B is a photograph of a set of blots for quantitative measurement of gene expression in electrically stimulated constructs produced according to an embodiment of the invention and non-stimulated constructs.

Eluted proteins are electroblotted in 1× Tris/Glycine/SDS running buffer (Bio-Rad) onto polyvinylidene difluoride membranes (Bio-Rad) at 100 V for 60 minutes at room temperature in a Bio-Rad Trans-Blot cell. Blots are first incubated with 5% nonfat dry milk at room temperature for 1 hour in PBS-T to block non-specific binding of antibodies and then, for an additional 1-2 hours, with the appropriate primary antibody. The primary antibodies are: (1) rabbit anti-Cx43 (Chemicon), diluted 1:10 in PBS-T; (2) goat anti-CK-MM (Biodesign), diluted 1:3,000 in PBS-T; (3) mouse anti-troponin I (Biodesign), diluted 1:3,000 in PBS-T; (4) mouse anti-α-MHC (ATCC) hybridoma supernatant; and (5) mouse anti-β-MHC (Chemicon), diluted 1:50 in PBS-T. Blots are washed five times with PBS-T and incubated 1 hour at room temperature with rabbit anti-goat, rabbit anti-mouse, or sheep anti-rabbit IgG antibodies (Sigma), respectively, all conjugated to horseradish peroxidase and diluted 1:10,000 in PBS-T. After five additional washes, the immunocomplexes are developed using enhanced horseradish peroxidase-luminol chemiluminescence (ECL Western blotting detection reagents, Amersham) and detected after exposure to photographic film (Hyperfilm-ECL) for 5-30 seconds. Band intensity is quantified by an image analysis software (Scion Image). FIG. 4A is a photograph of the protein bands, showing that the intensity of the protein bands from stimulated constructs is greater than that from non-stimulated constructs. The ratio of α-MHC to β-MHC after 3 days (pre-stimulation) was 1.5. For stimulated constructs, the ratio was 1.8 after 5 days, while the ratio was 1.4 for non-stimulated control constructs.

Gene Expression. Total RNA from the constructs is extracted using Trizol reagent (GibcoBRL) and RNeasy® mini kit (Qiagen) following manufacturer's instructions. Briefly, constructs in Trizol are shredded by steel-ball bead beater using 6 cycles of 25 rpm for 10 seconds each. The supernatant is collected after centrifugation at 14,000 rpm for 15 minutes. Total RNA is collected by RNA column chromatography using water as eluant. RNA concentration is determined by measuring the absorbance at 260 nm by UV spectrophotometry.

RT-PCR. One step RT-PCR is carried out as described (Qiagen). Total RNA (0.5-0.05 µg) is used with specific primers and the RT-PCR reactions are performed at 50° C. for 30 minutes, 95° C for 15 minutes, 23 cycles at 94° C. for 1 minute, 60° C. for 1 minute, 72° C. for 1.5 minute, and then 72° C. for 10 minutes. The different primers used in the PCR reactions are shown below.

```
Forward α-MHC:
5'-GGAAGAGCGAGCGGCGCATCAAGG-3'

Reverse α-MHC:
5'-CTGCTGGACAGGTTATTCCTCA-3'

Forward β-MHC:
5'-GCCAACACCAACCTGTCCAAGTTC-3'

Reverse β-MHC:
5'-TCAAAGGCTCCAGGTCTCAGGGC-3'

Forward Cx-43:
5'-CATTGGGGGGAAGGCGTGAGG-3'

Reverse Cx-43:
5'-AGCGCACGTGAGAGATGGGGAAG-3'

Forward GAPDH:
5'-TGGAAAGCTGTGGCGTGATG-3'

Reverse GAPDH:
5'-TCCACCACCCTGTTGCTGTAGC-3'

Forward integrin fβ:
5'-GCAGCAGCATCTTAGTCACAGTAGG-3'

Reverse integrin fβ:
5'-TTTGATTCTGTTTAACTAGTCCTGG-3'

Forward cardiac actin:
5'-CAGATCTTCTCCATGTCG-3'

Reverse cardiac actin:
5'-GGCTGGCTTTGCGGGTGA-3'
```

FIG. 4B is a picture comparing the amount of RNA for the above for non-stimulated and stimulated samples.

Example 4

Cell Viability Assessment

To detect viable cells at depths of up to 100 µm from the construct surfaces, the constructs are extensively washed in PBS and then incubated with calcein-AM (Molecular Probes), a substrate that is hydrolyzed by intracellular esterases to a fluorescent product that is retained by cells with intact membranes. Intact cells in constructs are visualized without further preparation using a confocal laser scanning microscope (MRC-500, Bio-Rad) equipped with an argon-krypton laser emitting monochromatic light at 488 nm. Optical sectioning is done using a 20× objective in 1.5-µm steps. Individual images are reconstructed into composite images (3D reconstruction analysis) using computer software (Bio-Rad).

Example 5

Metabolic Activity Assays

Metabolic activities of cells within constructs and ventricular tissues are assessed by the uptake and enzymatic reduction of the tetrazolium dye, 3-(4,5-dimethylthiazol-2-yl)-2,5-diphenyltetrazolium bromide (MTT, Sigma). Samples (2-15 mg wet wt) are rinsed with PBS and incubated with MEM (GIBCO-BRL) without phenol red and 0.5 mg/mL MTT for 4 hours on an orbital shaker at 37° C. and 60 rpm. Medium is replaced with an equal volume of 0.1 M HCl in absolute isopropanol and pipetted directly through the constructs to solubilize the resulting formazan crystals. After 10 minutes of incubation at 37° C., the absorbance is read at 570 nm, using a microplate spectrophotometer.

Example 6

Media Analysis

Physiological ranges of $PO_2$ (115-130 mmHg), $PCO_2$ (48-55 mmHg), and pH (7.21-7.33) are maintained for the duration of cultivation, as measured by a blood gas analyzer (IL 1610, Instrumentation Laboratory). Glucose and lactate concentrations are measured using a glucose/lactate analyzer (2300 StatPlus, YSI). The activity of LDH in the culture media is monitored using a LDH-L reagent kit (Chiron Diagnostics). Media samples are sonicated using a Sonic Dismembrator (Vibra-Cell, Sonics and Materials), and absorbance is measured at 340 nm (Spectronic 1001+, Milton Roy) against cell-free medium.

Example 7

Transmission Electron Microscopy

Figure 5C:
FIG. 5 is a series of electron micrographs of A) native heart tissue, B) stimulated construct produced according to an embodiment of the invention and C) non-stimulated construct.
Figure 5B:
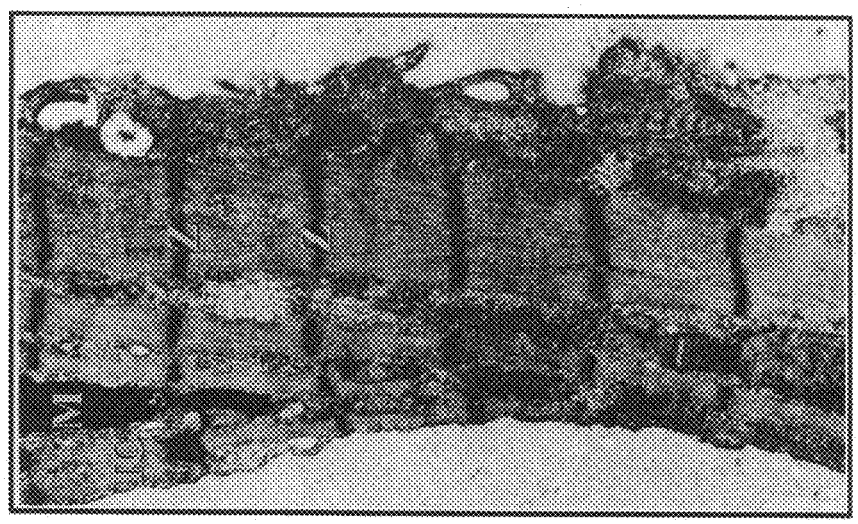
Figure 5A:
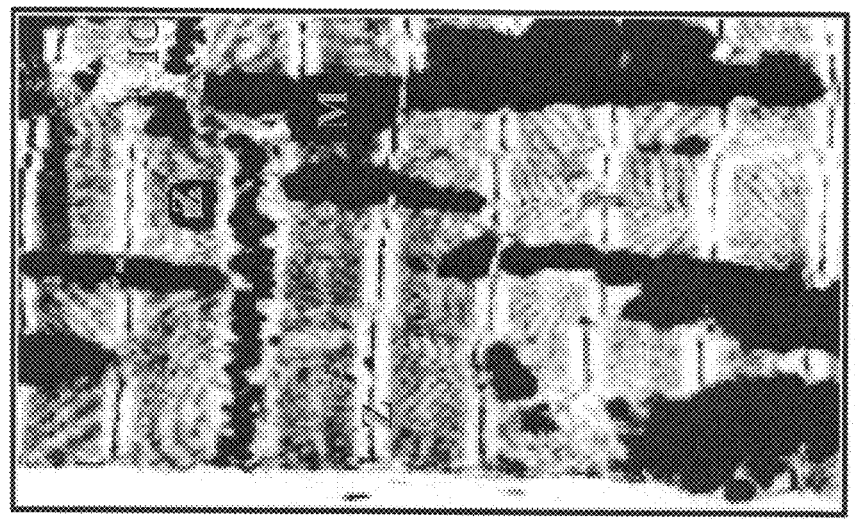

Samples are fixed in Karnovsky's reagent (0.1 M sodium cacodylate with 2% paraformaldehyde and 2.5% gluteraldehyde, pH=7.4), post-fixed in 1% osmium tetroxide in veronal-acetate buffer, dehydrated in graded ethanol in propylene oxide, and embedded in Epon 812 (Polysciences). Sections (70 nm thick) are prepared using a Leica Ultra Cut and a diamond knife, stained with lead citrate and uranyl acetate, and examined using a Philips EM410 transmission electron microscope operated at 80 kV. FIG. 5 is a series of transmission electron micrographs illustrating that stimulated tissue constructs (FIG. 5B) is more similar morphologically to native tissue (FIG. 5A) than are non-stimulated tissue constructs (FIG. 5C).

Example 8

Electrophysiological Assessment

An electrophysiological system was custom-designed to enable stimulation and recording of unipolar extracellular potentials in constructs and ventricular tissues under controlled environmental conditions using a linear array of electrodes. A cylindrical Plexiglas is tightly fitted inside an electrically grounded brass casing placed on a 37° C. heater (VWR). The brass case distributes the heat evenly through the chamber and serves as an electrostatic shield. The chamber is gassed with a prewarmed mixture of 5% $CO_2$ in air and filled with 50 mL of culture medium (DMEM with 15 mM HEPES, 4.5 g/L glucose), which is recirculated (at 60 mL/minute for constructs and 120 mL/minute for ventricular tissues) using a pulseless gear pump (Cole-Palmer). Temperature and pH are maintained at 37.0±0.1° C. and 7.32±0.02, respectively.

All microelectrodes are made of insulated tungsten wire and have uninsulated tips with diameters of 50±6 μm (Microprobe). Two electrodes for bipolar stimulation are positioned 200 μm apart and connected to a programmable cardiac stimulator (SEC-3102, Nihon Kohden). Eight recording electrodes are positioned 500 μm apart in a linear array, 1.5 to 5 mm from the stimulating site. Exact distances between electrodes are measured using a microscope and NIH 1.60 image analysis software. Shielded cables connect recording electrodes to bioelectric amplifiers (AB.601G, Nihon Kohden). A reference Ag—AgCl electrode (WPI) is placed in the medium 3.5 away from the microelectrode.

Samples are placed in a tissue holder 2-3 mm under the surface of the culture medium, secured using Teflon screws, and left to equilibrate for 15 minutes. An XYZ mechanical micropositioner (Taurusr, WPI) is used to gradually advance the microelectrode away toward either the top surface of the construct or the epicardial surface of the ventricle, and pacing impulses are simultaneously applied (3-5 V, 1-ms pulses at a rate of 60 beats/minute). The position of the array is fixed at the point where the amplitudes of the recorded responses appear maximal, and a recording protocol is performed as follows.

Spontaneous beating, if present, is recorded for 3-5 minutes. After 15 minutes, monophasic pacing pulses (1-ms duration) are applied at a rate of 60 beats/minutes, starting at a pacing voltage of 0.1 V, which is then increased in 0.1 V increments until the sample is captured (i.e., until each pacing impulse is followed by a recorded tissue response). The corresponding pacing voltage, defined as the excitation threshold, represents the lowest stimulus that produces a stable propagation (for at least 1 minute at a rate of 60 beats per minute) over the length of the recording array. For the next 20-30 minutes, the sample is continuously paced at a rate of 60 beats per minute using pacing amplitudes 1.5 times higher than the excitation threshold, and responses are recorded every 4-5 minutes for a period of 1 minute. The pacing rate is then increased every 5 minutes by 30 beats per minute, and responses to each rate are recorded for the last 40 seconds. The maximum pacing frequency at which the sample can be captured for at least 5 minutes is defined as the maximum capacity rate. After reaching the maximum capacity rate, stimulation is stopped for 10 minutes and then reapplied at 30 and 60 beats per minute for 5 minutes each to check for reproducibility of the recorded waveforms. At the end of the experiment, double and triple extra-stimuli and rapid stimulation at frequencies above the maximum capture rate are applied in an attempt to induce arrhythmia.

All recorded signals are amplified and band-pass filtered between 0.3 and 1,000 Hz. The unfiltered noise level is 35 μV, peak to peak, with virtually no 60-Hz component. Analog recordings are digitized at a sampling rate of 3 kHz using a 16-bit analog-to-digital board (AT-MIO-16X, National Instruments), real-time displayed using LabView data acquisition software, and stored and analyzed using MATLAB (The Mathworks).

Activation times at each recording electrode are determined as the minima of five-point derivatives of the low-pass filtered signals. The stimulus-activation time intervals at each electrode (conduction times) are plotted against the corresponding distances and fitted by linear regression. The conduction velocity of a propagated beat is calculated as the inverse slope of the best linear fit. The peak-to-peak (p-p) amplitudes of the responses are determined from linearly detrended signals around the activation times. Recording sites with very low or fractioned (polyphasic) activity are ignored.

For each tissue sample, p-p amplitudes at each electrode and conduction velocities are averaged from recording made during the initial 20 minutes of pacing at 60 beats per minute (i.e., over at least 200 beats). Conduction velocity, maximum amplitude, and average amplitude are calculated, respectively, as the averages of conduction velocities, maximum p-p amplitudes, and all p-p amplitudes from all samples within a group. The maximum and average amplitudes, respectively, represent local and spatially averaged properties of constructs or ventricles.

Example 9

Evaluation of Contractile Response

Figure 6:
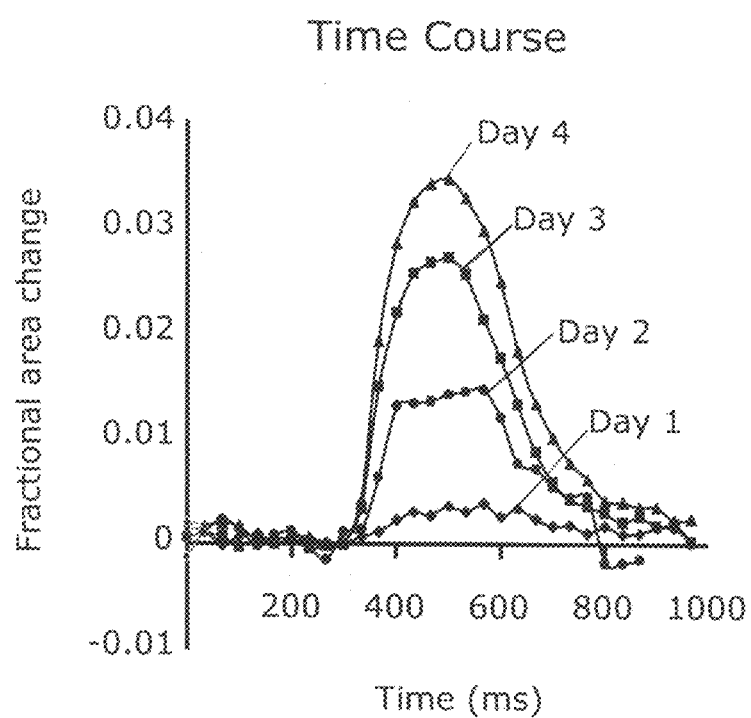
FIG. 6 is a graph showing the change fractional area change upon contraction with time for a construct produced according to an embodiment of the invention.

The contractile function of engineered cardiac constructs is evaluated by monitoring and videorecording contractile activity upon electrical stimulation at 10× magnification using a microscope (Nikon Diaphot). Each construct is placed in a 100 mm Petri dish containing 120 mL Tyrode's solution (140 mM NaCl, 5.4 mM KCl, 0.33 mM $NaH_2PO_4$, 1.8 mM $CaCl_2$, 1 mM $MgCl_2$, 5 mM HEPES, 5.5 mM D-Glucose, pH 7.4) between two custom made electrodes (carbon rods) connected to a cardiac stimulator (Nihon Kohden). The temperature is maintained at 37° C. using a heating tape (VWR) attached to the bottom of the Petri dish. The stimuli (square pulses, 2 ms duration) are applied at a rate of 60 bpm starting at an amplitude of 1 V that is gradually increased at increments of 0.1 V until the excitation threshold (ET) is reached and the entire construct is observed to beat synchronously. The maximum capture rate (MCR) is defined as the maximum pacing frequency for a synchronous stimulus-response of the constructs. To measure MCR, the stimulation frequency is increased from 60 to about 600 bpm with a minimum step size of 10 bpm, at a constant voltage that is equal to either 150% or 200% of the excitation threshold until the construct contractions become asynchronous or irregular or completely ceased. For evaluation of contraction amplitude, video recorded beating sequences (1-5 minutes) are digitized at the rate of 30 frames per second. The "face-sectional" area of each construct is determined as a function of time using image analysis software (Scion Image). Amplitude of contraction is expressed as fractional area change. FIG. 6 illustrates the increase in the fractional area of stimulated samples over time.

Example 10

Cardiac Differentiation of Embryonic Stem Cells by Electrical Stimulation

Embryonic stem cells are grown using previously established approaches such as those described by Itskowitz-Eldor et al. (Mol. Med. 2000, 6: 88-95). The cells are grown in monolayers in DMEM medium containing 20% FBS, in a humidified 5% $CO_2$/air 37° C. environment. Cells are passaged every 6 or 7 days after 70% confluence is reached. After each passage, adherent cells are detached by trypsin digestion, and the cell number and viability are assessed.

Cells are then prepared in form of a cell suspension in Matrigel ($10^6$ cells/5 µL Matrigel) as described above for cardiac myocytes. The Matrigel suspension is seeded onto a Ultrafoam™ collagen sponge scaffold (6×8×1.5 mm), which was first hydrated in culture medium (DMEM) for 2 hours and blotted dry. The cell-Matrigel mixture is loaded to the scaffold, at the initial cell density of $8×10^7$ cells/mL scaffold volume (using 60 µL of cell-Matrigel suspension per scaffold).

The construct is placed into a 6-well plate (one construct per well) and transferred to an incubator (humidified 5% $CO_2$, 37° C. environment) for 20 minutes in order for the gel to harden. Cardiac differentiation medium (DMEM, 10% FBS, 1% Pen/Strep, 1% HEPES) is then added (5 mL per well) and the construct is cultured on an orbital shaker at 25 rpm for 3 days. On Day 4, the construct is transferred into the stimulation chamber (a culture chamber equipped with the stimulation electrodes, as described above for the cultivation of cardiac myocytes). The electrical stimulation is applied for 7-8 days at a frequency between 60 and 180 bpm (1-3 Hz) and an amplitude of 5 V.

Cardiac differentiation is assessed on-line, without interrupting the cultivation, by measuring the contractile responses (contractile amplitude, frequency) as described above for cardiac myocytes). Tissue constructs are harvested at timed intervals and processed histologically and immunohistochemically for overall evaluation and to assess the presence and distribution of cardiac specific markers (H&E staining, troponin I, connexin-43, α-MHC, β-MHC). The same markers are determined using immunoblots and RT-PRC. Metabolic rates (glucose consumption and lactate production) and LDH (an indicator of cell damage) are measured biochemically from medium samples. Total DNA and protein are measured biochemically in harvested constructs as described above for cardiac constructs prepared with cardiac myocytes. Early cardiac progenitor markers (MEF2-C, Nkx2.5, GATA 4, TEF-1) and cardiac markers expressed later during the development (MEF2-A, MEF2-D) are determined by RT-PCR.

Example 11

Perfusion of Constructs

Gel-cell inoculated scaffolds were placed between two stainless steel screens and two silicone gaskets in 1.5-mL polycarbonate perfusion cartridges (one scaffold per cartridge) (Millipore, Bedford, Mass.). The screens (85% open area) provided mechanical support during perfusion, and the gaskets (1 mm thick, 10 mm OD, 5 mm ID) routed the culture medium directly through the construct. Each seeding loop containing one perfused cartridge was placed onto a push/pull syringe pump as shown in FIG. 1A.

Each cartridge was connected to two 80-cm-long coils of 1.6 mm ID, 3.2-mm OD platinum-cured silicone tubing serving as gas exchangers, and two 1 0-mL syringes serving as medium reservoirs, sampling ports, and for de-bubbling. Cartridges were completely filled with culture medium, with the use of a pair of 3-mL syringes, one full and one empty, connected to the circuit at the inlet and outlet of the cartridge via 3-way stopcocks. The total volume of medium in the cartridge, tubing, and reservoir syringes was 8 mL (1.5 mL in the cartridge, 4 mL in the tubing, 2.5 mL in one syringe, and the other syringe was empty). Any air bubbles were displaced by culture medium injected from the de-bubbling syringe 38a into the downstream syringe 38b. The seeding set-up was placed in a 37° C./5% $CO_2$ incubator, and the pump was programmed to the set flow rate, with the reversal of flow direction after 2.5 mL was perfused in a given direction. All components (cartridges, screens, gaskets, tubing) were steam sterilized for 30 min. Cartridges were subjected to alternating flow perfusion for the first 1.5 hours to prevent washout of cardiomyocytes before they attached to the scaffold and then to unidirectional perfusion for an additional 7 days (FIG. 1B).

The unidirectional perfusion apparatus included one channel of a multichannel peristaltic pump 50 (Cole Parmer, Vernon Hills, Ill.), a gas exchanger 52 (a 3 m coil of thin silicone tubing), a reservoir bag 54, and two syringes 56a and 56b. The total volume of medium was 32 mL. The flow rate was set at 0.5 mL/min, corresponding to an interstitial velocity of 500 micron/s and maintained throughout the cultivation. The culture medium was DMEM (4.5g/L glucose) supplemented with 10% FBS, 10 mM HEPES, 2 mM L-glutamine, and 100 U/mL penicillin (all from GIBCO-BRL). Control constructs were cultivated in orbitally mixed dishes (25 rpm).

Analytic methods. Constructs and culture medium were sampled immediately postseeding and after 1.5 h, 1 day, and 7 days of culture. Cell number, viability, metabolism [lactate yield on glucose (L/G)], and cell cycle were assessed at all time points; cell distribution, the presence of contractile proteins, and contractile function were assessed at 7 days. A total of 26 rat litters (~260 heart ventricles) was used in 10 independent experiments, with n=2-8 constructs/data point.

Statistical analysis. Individual and interactive effects of culture system and time were determined using two-way ANOVA (SigmaStat). The culture system was investigated at two levels (orbital shaker at 25 rpm; perfusion of 0.5 ml/min); the effect of time was investigated at three levels (1.5 h, 1 day, and 7 days) with respect to live cell number, cell viability, glucose consumption rate, and the molar ratio of lactate produced to glucose consumed. For cell cycle fractions, the effect of time was investigated at two levels (1 and 7 days). All experimental data passed normality and equal variance tests. For pairwise comparisons, we chose the most conservative Tukey's post hoc test with $P<0.05$ considered as significant.

Cell number and viability. Cell number and viability were assessed using ethidium monoazide bromide (EMA) in conjunction with fluorescence-activated cell sorting (FACS) as previously described (25). In brief, EMA was added to aliquots of freshly isolated neonatal rat cardiomyocytes or constructs (10 µl of 50 µg/ml solution per $1×10^6$ cells suspended in 100 µl PBS) in six-well dishes that were placed on ice under fluorescent light for 10 min to allow for EMA to cross-link to DNA of nonviable cells. EMA-labeled constructs were digested with collagenase and dispase (10 ml of solution containing 0.6 mg/ml collagenase type II with 282 U/mg and 1.2 U/ml of dispase in culture medium per construct) for 30 min at 37° C. and 30 min on ice, with periodic pipetting to dissociate cell aggregates. EMA-labeled dissociated cells were rinsed with culture medium and counted using a hemocytometer (VWR). Cells were resuspended in PBS at the concentration of 106 cells/ml and subjected to FACS (FACScan, Becton-Dickinson). The change in cell viability was calculated as the difference between the measured viabilities of freshly isolated cells and cells harvested from digested constructs. As an independent measure of cell damage and death, a lactate dehydrogenase (LDH) assay was performed on samples of culture medium after 1, 3, and 7 days of culture using a commercial kit (Chiron Diagnostics; East Walpole, Mass.), as described in Example 2.

Cell survival was consistent with the conditions of flow in each experimental group. Flow visualization demonstrated that the central 5-mm-diameter region of the perfused constructs had uniform interstitial flow, whereas the outer edge ring between the two gaskets was shielded from flow (FIG. 1A). In orbitally mixed dishes used as a control, fluid flow was generated at construct surfaces but not in their interiors.

The effects of culture system and time of culture on cell survival and function are shown in FIG. 7; the corresponding statistical data are shown in Table 1. In seeded constructs (1.5-h time point), the live cell numbers were comparable for perfused and control constructs (~7 million cells/construct in both groups; FIG. 7A). Throughout the cultivation (1- and 7-day time points), the number of live cells in perfused constructs was significantly higher than that in dish-grown constructs (FIG. 7A). Notably, the number of live cells in dish-grown constructs decreased rapidly during the first day of culture and continued to decrease relatively slowly between days 1 and 7. In contrast, live cell numbers in perfused constructs did not change from 1.5 h to day 1 and decreased slowly over the time of culture. The volume fraction of the construct that was adequately perfused corresponded roughly to the fraction of cells that remained viable over 7 days of culture (FIG. 7A). Cell viability was significantly higher in perfused than dish-grown constructs at all time points (FIG. 7B). Importantly, the final cell viability in perfused constructs (81.6±3.7%; FIG. 7B) was not significantly different from the viability of the freshly isolated cells (83.8±2.0%), and it was markedly and significantly higher than the cell viability in dish-grown constructs (47.4±7.8%; FIG. 7B). The overall level of cell damage and death was assessed by monitoring the levels of LDH activity in the culture medium. At all time points tested (1, 3, and 7 days), the levels of LDH were significantly lower in perfused constructs compared with the orbitally mixed dish (FIG. 7E), indicating less cell damage and death.

TABLE 1

P Values for individual and interactive effects of culture time and culture system on cell viability and metabolism

|  | Live Cell Number | Cell Viability | L/G | Glucose Consumption | LDH |
| --- | --- | --- | --- | --- | --- |
| Culture time | <0.001 | <0.002 | <0.001 | <0.001 | NS |
| Culture system | <0.001 | <0.001 | 0.003 | 0.035 | <0.001 |
| Culture time × system | NS | 0.035 | 0.038 | NS | NS |

Values were determined by two-way ANOVA in conjunction with Tukey's post hoc test.
P < 0.05 was considered significant.
L/G, lactate-to-glucose ratio;
LDH, lactate dehydrogenase,
NS, not significant Cell metabolism. Cell metabolism was assessed from the molar ratio of lactate produced to glucose consumed (L/G; ideally, 1 mol/mol] for aerobic metabolism and 2 mol/mol for anaerobic metabolism). Glucose and lactate concentrations were measured in 15 culture medium sampled at timed intervals using a glucose and L-lactate analyzer (model 2300 STAT Plus, Yellow Springs Instruments; Yellow Springs, Ohio).

Figure 7A:
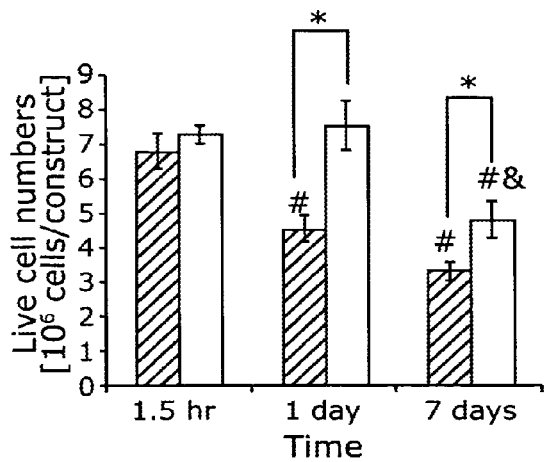
FIG. 7 is a series of graphs comparing, for perfused constructs (open bars) and control constructs (filled bars) with respect to time, A) live cell number per construct; B) viability of cells on the construct (Dashed line represents the viability of freshly isolated cells: 83.8+/−2.0 (n=6); C) molar ration of lactate produced to glucose consumed; D) glucose consumption rate in micromoles per hour per $10^6$ cells (Dashed line represents reported values of the glucose consumption rate, Casey, et al., *Circulation*, 102: 3124-3129, 2000); E) lactate dehydrogenase (LDH) content (in units) in culture medium (P values were calculated by two-way ANOVA in conjunction with Tukey's test for pair wise multiple comparisons (n=3-9 samples per data point). Differences were considered significant if P<0.05. *Significant difference between perfused and dish-grown constructs; #significant difference between 1- and 7-day or 1.5 hour constructs; &significant difference between 7- and 1-day constructs)
Figure 7B:
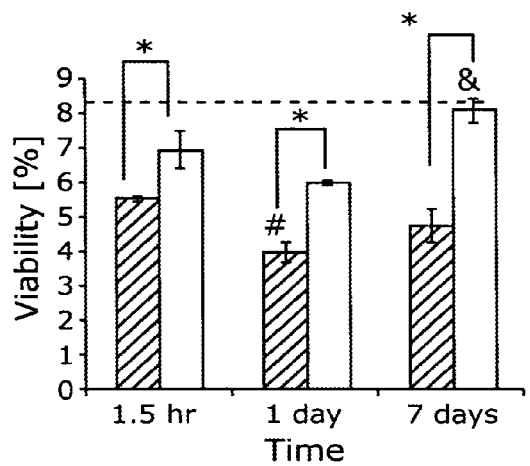
Figure 7C:
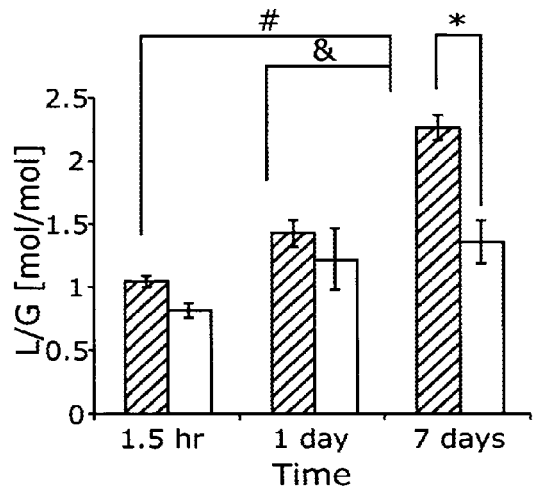
Figure 7D:
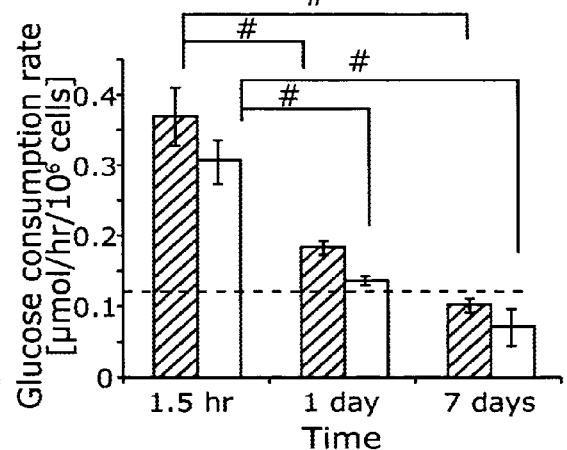
Figure 7E:
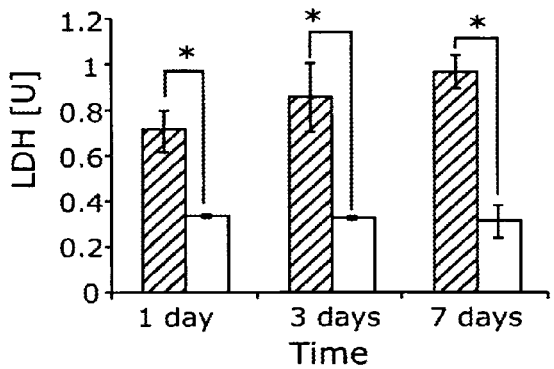

The $P_{O_2}$ in culture medium was significantly higher at the inlet of perfusion cartridges than in orbitally mixed dishes (145±1 vs. 135±1 mmHg, P<0.05, n=5-8). The measure decrease in oxygen tension across the perfused cartridge was only 8 mmHg, suggesting that culture medium rich in oxygen was available to the cells throughout the construct volume. In contrast, culture medium rich in oxygen was available only to the cells at surfaces of dish-grown constructs. The molar ratio of lactate produced to glucose consumed (L/G) was ~1 for perfused constructs throughout the duration of culture, indicating aerobic cell metabolism (FIG. 7C). In contrast, L/G increased progressively from 1 to ~2 with time of culture for dish-grown constructs, indicating a transient to anaerobic cell metabolism. (FIG. 7G). The increase in L/G with time in dish cultures was statistically significant (P<0.001). The consumption rate of glucose, the primary energy source in our system, per unit live cells was not significantly different between the groups at any time point. It decreased after seeding to values that were comparable at 1 and 7 days of cultivation and consistent with previously published data (8) (FIG. 7D).

Individual and interactive effects of culture system and culture time on cell viability and metabolic function. Importantly, both the culture system (perfusion or orbital dish) and time of culture (1.5 h, 1 day, and 7 days) had statistically significant individual effects on the cell survival parameters shown in FIG. 7 (live cell number, cell viability, L/G, glucose consumption). The culture system alone had a significant effect on the levels of LDH in culture medium. For cell viability and L/G, we detected additional interactive effects of culture system and culture time (Table 1).

Cell cycle analysis. For cell cycle analysis, constructs were digested, and cells were pernneabilized in 70% ethanol (1 mil06 cells) for 30 min at 4° C. After centrifugation (10 min, 1,000 rpm), the pellet was resuspended in a solution of 50 µg/ml RNase A and 0.1% Triton X-100 in PBS (0.5 ml/$10^6$ cells) to digest double-stranded RNA, which might interfere with staining. Propidium iodide was added (50 µg/ml), and the cell suspension was subjected to FACS (FACScan, Becton-Dickinson) to determine the fraction of cells in the $G_0/G_1$, S, and $G_2/M$ phases. Peak deconvolution was performed using ModFit LT V2.0 for Macintosh.

Figure 8A:
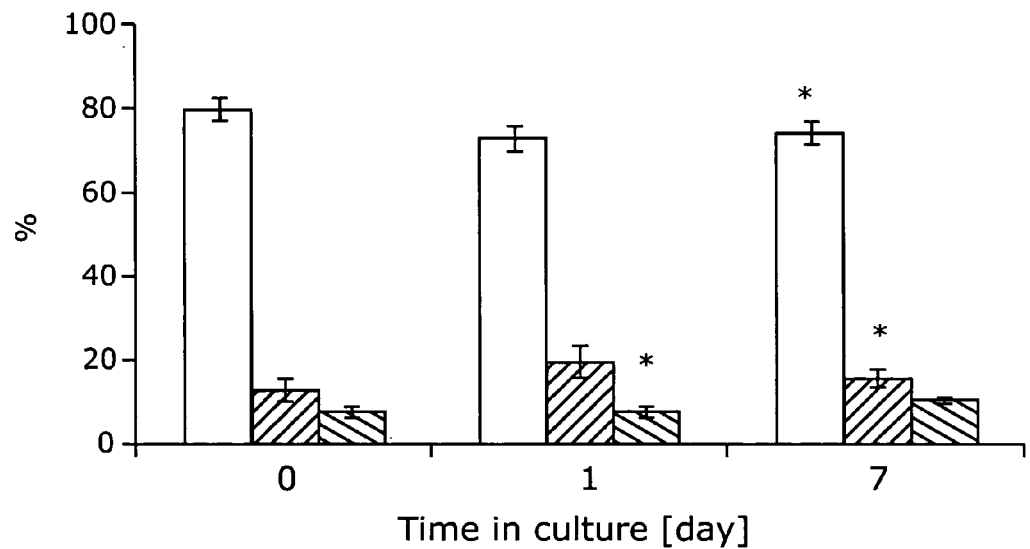
FIG. 8 is a series of graphs showing, with respect to time, tie fraction of cells from A) perfused constructs and B) dish-grown constructs, the fraction of cells in the $G_0/G_1$ (open bar), S (light gray bar) and $G_2/M$ (dark gray bar) phases of the cell cycle. (P values calculated as for FIG. 7; #Significant difference between the fractions of cells within the orbital dish group; *Significant difference between the corresponding perfused and dish-grown constructs).
Figure 8B:
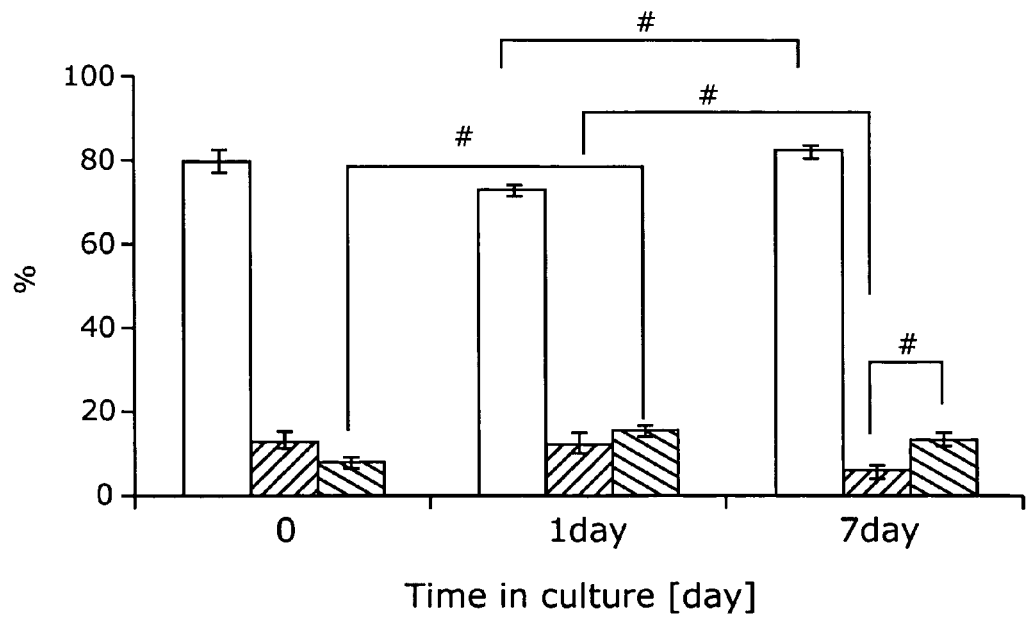

Cell cycle analysis of the mononucleated cell fraction indicated that there was a proliferative cell compartment in both perfused and dish-grown constructs (FIG. 8). The relative fractions of cells in the $G_0/G_1$, S, and $G_2/M$ phases determined for the initial cell population (time 0 in FIGS. 8, A and B) were maintained throughout the duration of culture in perfused but not dish-grown constructs. Cells isolated from perfused constructs and freshly isolated cardiomyncytes had more cells in the S phase than in the $G_2/M$ phase, whereas cells isolated from dish-grown constructs appeared unable to complete the cell cycle and accumulated in the $G_2/M$ phase. After 7 days of culture, the percentage of cells in the S phase was significantly higher in perfused than dish-grown constructs (FIG. 8). Statistical analysis demonstrated significant effects of culture system on fractions of cells in the S phase (P=0.005) and $G_2/M$ phase (P=0.01) and culture time on the fraction of cells in the $G_0/G_1$ phase (P=0.018).

Histological evaluation. For histological evaluation, constructs were paraffin embedded, bisected, cross sectioned (5

µm thick), and either stained with hematoxylin and eosin or immunostained as described in Example 2 with monoclonal antibodies for sarcomeric α-actin (diluted 1:500, Sigma), cardiac troponin I (diluted 1:150, Biodesign), or sarcomeric tropomyosin (diluted 1:100, Sigma).

Figure 9:
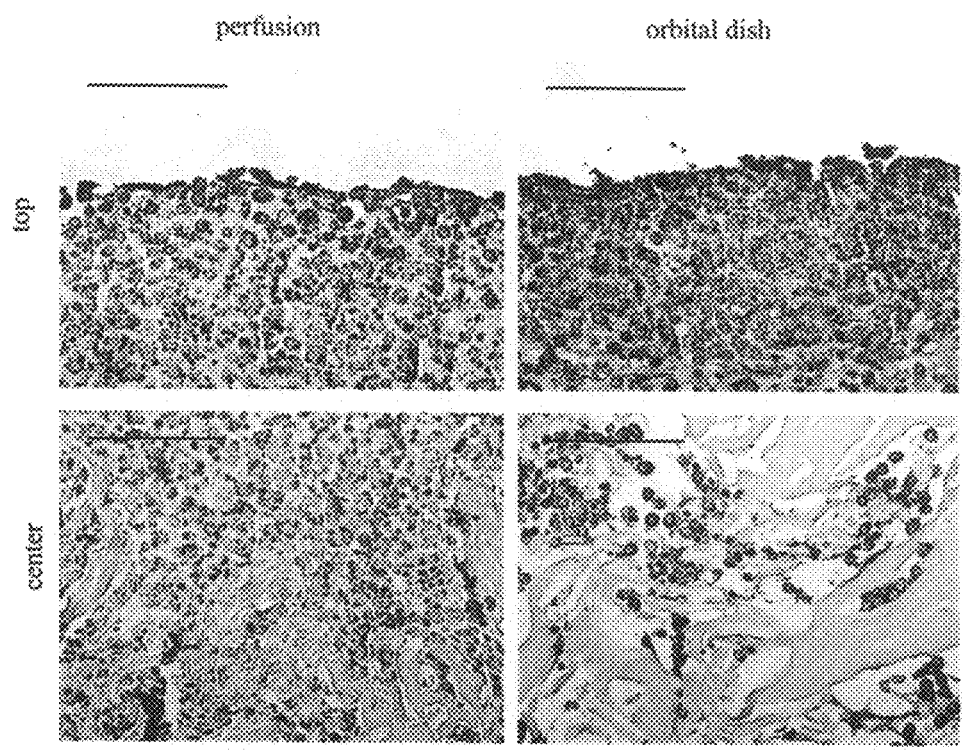
FIG. 9 is a set of micrographs illustrating the distribution of sarcomeric alpha-actin expressing cells at the periphery (top) and in the interiors (bottom) of constructs cultivated in perfused cartridges (left) or in orbitally mixed dishes (right) (scale bar=100 micron).

After 7 days of culture, the overall tissue architecture appeared markedly better for perfused than dish-grown constructs. The 100- to 200-µm-thick peripheral layers of constructs from both groups consisted of tightly packed cells containing cardiac differentiation markers in contrast to construct interiors, which were markedly different (FIG. 9). Medium perfusion maintained high and spatially uniform cell density throughout the construct volume (except in the outer edge regions shielded from fluid flow), whereas molecular diffusion in the interiors of dish-grown constructs supported only a low density of scattered cells.

Figure 10A:
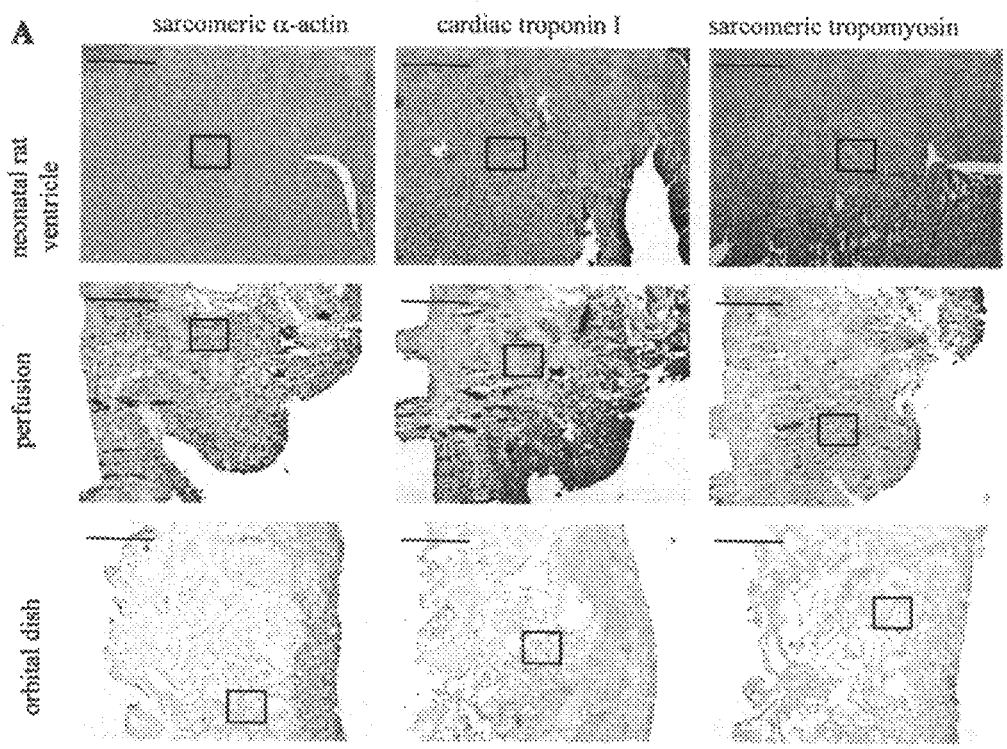
FIG. 10 is a set of micrographs illustrating A) tissue architecture and B) cell differentiation through immunohistochemical staining of three contractile proteins in native neonatal rat ventricles and 7-day constructs seeded and cultured either in perfused cartridges or in orbitally mixed dishes (A: scale bar=300 micron); the images in B (scale bar=50 micron) are higher magnification views of the areas in the boxes in A.
Figure 10B:
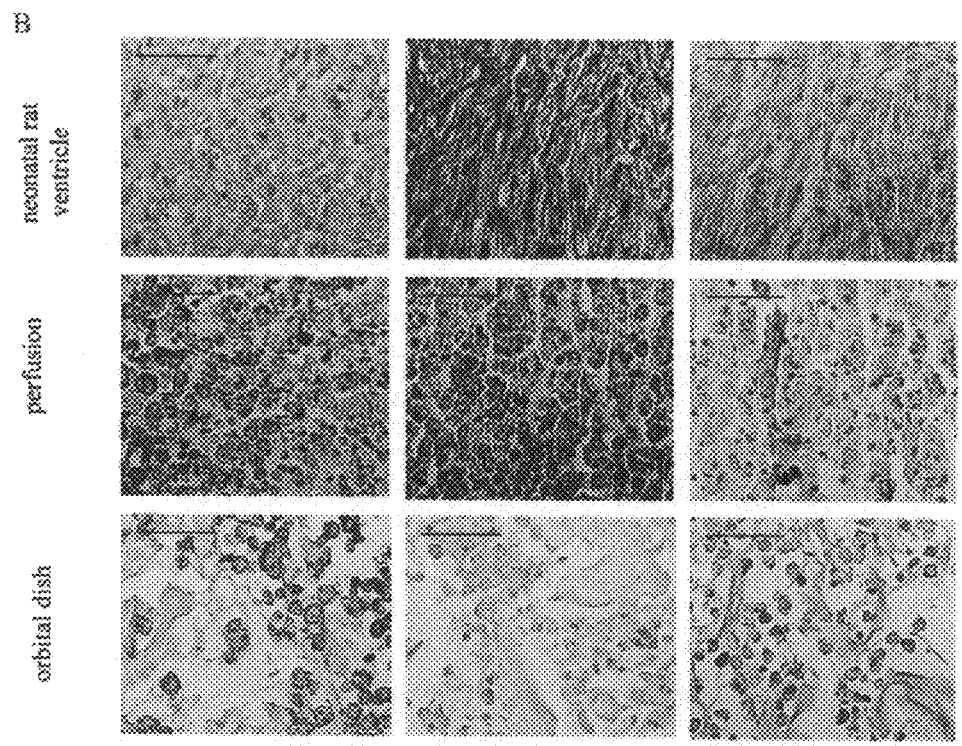

Sarcomeric α-actin, cardiac troponin I, and sarcomeric tropomyosin were present throughout the perfused construct volume (FIGS. 10, A and B). In contrast, dish-grown constructs exhibited spatially nonuniform cell distributions, with most cells expressing contractile proteins located within a 100- to 300-µm-thick surface layer and only a small number of viable differentiated cells in the construct interior (FIGS. 10, A and B). Constructs from both groups consisted mainly of mononucleated cells and exhibited a lack of well-established structural alignment of the contractile proteins that was observed in native tissue. The central perfused regions of the constructs (5 mm diameter×1.5 mm thick) consisted of tightly packed cells containing sarcomeric α-actin, cardiac troponin I, and sarcomeric iropomyosin, similar to neonatal rat ventricles, and distinctly different from the tissue present in the centers of dish-grown constructs (5 mm diameter×1.5 mm thick), which contained only isolated and poorly differentiated cells (FIG. 10B).

Contractile function. The contractile function of engineered cardiac constructs was evaluated by monitoring contractile activity upon electrical stimulation at ×10 magnification using a microscope (Nikon Diaphot). Each construct was placed in a 100-mm petri dish containing 120 ml Tyrode solution (140 mM NaCl, 5.4 mM KCl, 0.33 mM $NaH_2PO_4$, 1.8 mM $CaCl_2$, 1 mM $MgCl_2$, 5 mM HEPES, and 5.5 MM D-glucose; pH 7.4) between two custom-made gold electrodes connected to a cardiac stimulator (Nihon Kohden). The temperature was maintained at 37° C. using a heating tape (VWR) attached to the bottom of the petri dish. The stimuli (square pulses, 2-ms duration) were applied at a rate of 60 beats/min starting at an amplitude of 1 V, which was gradually increased in 0.1-V increments until the excitation threshold (ET) was reached and the entire construct was observed to beat synchronously.

The maximum capture rate (MCR) was defined as the maximum pacing frequency (in beats/min) for a synchronous stimulus response of the constructs. To measure MCR, the stimulation frequency was increased (from 60 to 600 beats/min, in 20 beats/min increments) at a constant voltage (equal to either 150% or 200% of the ET). The construct response was measured at each frequency, and the frequency was increased until the contractions became asynchronous, irregular, or completely ceased. The maximum frequency for synchronous contractions was recorded as the MCR. The value of ET, which was different from one construct to another due to the differences in their structures, served as the baseline voltage for the measurement of MCR.

Constructs cultured in perfused cartridges were compared with constructs cultured in mixed dishes and to neonatal rat ventricles (full thickness slices obtained by bisecting the left ventricle parallel to the base apex line). The effect of palmitoleic acid (PA), a gap junction blocker (4), was investigated by incubating constructs or slices of native ventricles in PA (8.3 mM in Tyrode solution) for 20 min at 37° C. and then determining ET and MCR as described above. To test whether the effect of PA was reversible, constructs were transferred to Tyrode solution and retested after an additional 20 min at 37° C.

Spontaneous contractions were observed in some constructs early in culture (dish-grown constructs 2-3 days after seeding) and ceased after ~5 days of cultivation. At the end of cultivation (day 7), spontaneous contractions were not observed in either group of constructs. In response to electrical stimulation (e.g., at 5 V and 60 beats/min), constructs from both groups were reproducibly induced to contract synchronously. However, in perfused constructs the contraction frequency was constant, whereas in dish-grown 5 constructs the contraction frequency spontaneously increased every 1 to 2 min and the contraction pattern appeared arrhythmic. The ET was significantly lower in perfused than dish-grown constructs, and all construct ETs were significantly higher than those measured for neonatal rat ventricles. There was no significant difference in the MCRs measured for the two groups at suprathreshold stimulus amplitudes (150% and 200% ET; Table 2).

TABLE 2

Contractile Properties of Neonatal Ventricle, 7-Day Perfused Constructs, and 7-Day Dish-Grown Constructs

|  | Neonatal Rat Ventricle | Perfused Construct (7 days at 500 µm/s) | Dish-grown Construct (7 days at 25 rpm) |
|---|---|---|---|
| ET, V |  |  |  |
| Before PA | 1.1 +/− 0.1 | 3.3 +/− 0.2$^a$ | 4.5 +/− 0.4$^{ab}$ |
| After PA | 1.5 +/− 0.1 | 3.5 +/− 0.1$^a$ | 4.4 +/− 0.1$^{ab}$ |
| MCR at 150% ET, beats/min |  |  |  |
| Before PA | 413 +/− 7 | 420 +/− 30 | 502 +/− 32 |
| After PA | 465 +/− 15 | 415 +/− 35 | 378 +/− 31$^c$ |
| MCR at 200% ET, beats/min |  |  |  |
| Before PA | 427 +/− 40 | 415 +/− 45 | 523 +/− 14 |
| After PA | 427 +/− 58 | 435 +/− 45 | 380 +/− 31$^c$ |

Values are means +/− SE. Excitation threshold (ET) was measured at a stimulation frequency of 60 beats/min. The maximum capture rate (MCR) was measured at voltages equivalent to 150% and 200% ET. Data were collected before the treatment with palmitoleic acid (before PA) and after the washout of palmitoleic acid (After PA) Constructs could not be induced to contract in the solution containing PA. P values were calculated by one0way ANOVA in conjunctionwith Tukey's test for pair-wise multiple comparisons (N = 2–6). Differences were considered statistically significant if P < 0.05.
$^a$Significant different between constructs and neonatal rat ventricles;
$^b$significant difference between perfused and dish-grown constructs;
$^c$significant difference before and after PA treatment.

Upon incubation with PA, a gap junction blocker, synchronous construct contractions could not be induced even at 9.9 V. Contractile activity resumed after the washout of PA. The MCRs of perfused constructs and neonatal ventricles were similar to those recorded before PA treatment, suggesting that the effect of PA was completely reversible. However, the MCRs of dish-grown constructs failed to recover their baseline levels after PA washout (Table 2).

Example 12

Electrical Stimulation of a Construct Seeded with Mesenchymal Stem Cells

Unprocessed bone marrow was obtained from Clonetics (Santa Rosa, Calif.) from human donors without identifiers. Each 25-cm$^3$ harvest was diluted in 100 ml of isolation medium (RPMI 1640 supplemented with 5% FBS, Gibco, Carlsbad, Calif.), and cells were separated by density gradient centrifugation (Meinel, et al., 2003, Ann. Blomed. Eng., 32: 112-122). 20 ml aliquots of bone marrow suspension were overlaid onto a Sodium Diatrizoate Poly-sucrose Gradients (1.077 g/cm$^3$, Histopaque, Sigma, St. Louis, Mo.) and centrifuged at 800 g for 30 min at room temperature. The cell layer was removed, washed in 10 ml isolation medium, and pelleted, and the red blood cells were lysed in 5 ml of PureGene Lysis solution (Sigma, St. Louis, Mo.). Cells were separated, resuspended in expansion medium (DMEM supplemented with 10% FBS and 1 ng/ml bFGF, Gibco, Carlsbad, Calif.) and seeded in T75 flasks at a density of 5×10$^4$ cells/cm$^2$. The adherent cells were allowed to reach approximately 80% confluence (12-17 days for the first passage). Cells were trypsinized, plated and the second passage (P2) cells (80% confluence after 7 days) were used.

The expression of surface antigens (CD44, CD31, CD34, CD71, and CD105) in P2 cells was determined by FACS analysis (Meinel, et al., 2003, Ann. Biomed. Eng., 32: 112-122). Briefly, 50 µl aliquots of cell suspension (1×10$^7$ cells/ml) were incubated with 2 µl of each of the following antibodies: anti-CD44 conjugated with fluoresceine isothiocyanate (CD44-FITC), anti-CD31 conjugated with phycoerythrin (CD31-PE), anti CD34 conjugated with allophycocyanine (CD34-APC), anti CD71-APC, and anti-CD105 with a secondary rat-anti mouse IgG-FITC (all from Pharmingen, San Diego, Calif.). Cells were suspended in 100 µl of 2% formalin for FACS analysis.

Collagen scaffolds were discs cored from sheets of Ultrafoam® collagen hemostat (Davol Inc., Cranston R. I.), a water-insoluble, partial HCl salt of purified bovine dermal (corium) collagen formed as a sponge with interconnected pores. For cultivation with electrical stimulation, MSCs were inoculated into collagen sponges (Ultrafoam™, 6×8×1.5mm, 5·10$^6$ cells per scaffold) using diluted Matrigel® (BD Biosciences, Palo Alto, Calif.) (25 µl; 1:2 in culture medium) as a delivery vehicle. The constructs were placed in orbitally mixed dishes (25 rpm, one construct per well in 4 ml of culture medium) and stimulated in a spatially uniform electrical field between two parallel electrodes using suprathreshold square biphasic pulses (2ms duration, 1 Hz, 5 V). The conditions of stimulation were selected form the physiological range for native heart muscle and designed to induce synchronous contractions of cultured constructs. The stimulation was initiated after 12 hr to 1 day following scaffold seeding and applied for up to two weeks.

Figure 11A:
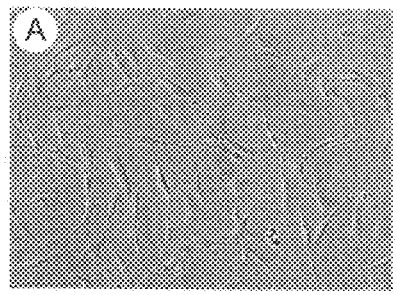
FIG. 11A is a phase contrast micrograph of P2 mesenchymal stem cells (MSC) at approximately 60-70% confluence. Original magnification 20×.
Figure 11B:
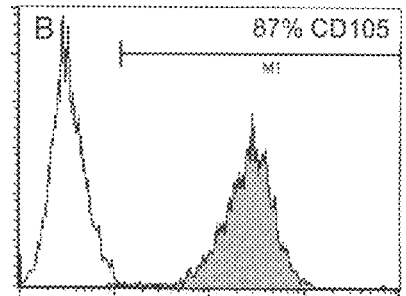
FIG. 11B is a graph showing the expression of CD105 surface marker in P2 MSC.

Expanded MSC exhibited fibroblast-like morphology (FIG. 11A). More than 90% of the cells expressed the surface antigen CD105/endoglin, a putative marker for mesenchymal stem cells (FIG. 11B). Negative expression of surface antigens CD34 and CD31 suggested the absence of hematopoietic progenitor cells and cells of endothelial origin. Most cells expressed CD71, a surface antigen commonly present in proliferating cells, and CD44, the transmembrane hyaluronate receptor for osteopontin, ankyrin, and fibronectin (Table 3).

TABLE 3

FACS analysis of human mesenchymal stem cells isolated from bone marrow

| Antigen | Cell surface marker/identified cell type | Passage 1 Average expression | Passage 2 Average expression |
|---|---|---|---|
| CD34 | Sialomucin/hematopoietic progenitors | − | − |
| CD31 | PECAM-1/endothelial cells | − | − |
| CD71 | Transferring receptor/proliferating cells | + | + |
| CD44 | Hyaluronate receptor/various cells | ++ | ++ |

Note:
10,000 cells of passage 1 and passage 2 cells expanded from bone marrow have been measured, donated from two different donors.
−, negative, defined as a fluorescence intensity < 2% of the isotype control;
+, fluorescence intensity 25–50% of the isotype control;
++, fluorescence intensity 70–90% of the isotype control.

Figure 12A:
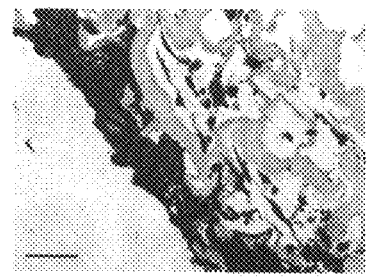
FIG. 12 is a set of micrographs showing the expression of A) cardiac troponin I and B) connexin 43 (connexin: green; nuclei: blue) in human MSC seeded on collagen sponges after two weeks of culture with electrical stimulation (5V, 60 bpm, biphasic pulses 2 ms in duration). Scale bar=50 micron.
Figure 12B:
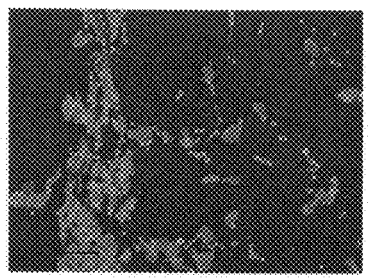

To test the feasibility of directed differentiation of MSC towards cardiac cell lineages, MSC were inoculated into collagen sponges (6 mm×8 mm×1.5 mm patches, 5·10$^6$ cells per scaffold delivered using Matrigel®) and cultured with the application of cardiac-like electrical stimulation. The constructs were placed in orbitally mixed dishes, cells were allowed to attach for 12 hrs, and electrical stimulation was initiated and applied continuously for up to 2 weeks (biphasic pulses, 2ms in duration, amplitude of 5V, constant frequency of 1 Hz); nonstimulated otherwise identical constructs served as controls. Like in native myocardium, electrical stimulation at a supra-threshold amplitude and constant frequency caused synchronous macroscopic contractions of cultured tissue constructs. After 4 days in culture, cells at the construct edges started to respond to pacing, presumably due to cell coupling. Immunostaining for cardiac troponin I and connexin 43 (gap junction protein) revealed a number of positive cells (FIGS. 12A, B); immunostains for cartilage markers were negative. These initial data suggest that biophysical signals that are physiological in nature, magnitude and regime of application fort native myocardium can potentially direct the differentiation of human MSC towards cardiac cell lineages.

What is claimed is:

1. A method for producing a three-dimensional tissue-engineered construct comprising:
    inoculating a three-dimensional substrate with a cell-gel suspension containing mammalian cells, thereby forming a cell-seeded construct;
    subjecting the cell-seeded construct to alternating flow perfusion through the construct immediately after the inoculating;
    supplying the cell-seeded construct with nutritive medium;
    cultivating the cell-seeded construct under conditions of direct medium perfusion, wherein the direct medium perfusion perfuses nutritive medium through the construct and provides substantially uniform cell density throughout the cell-seeded construct at depths greater than about 100 microns up to about 5 mm, except in regions shielded from medium flow;
    and, during cultivation, submitting the cells within the cell-seeded construct to a biomimetic electrical stimulation, the cultivating of the cell-seeded construct and biomimetic electrical stimulation extending for a time period to form a three-dimensional cell structure exhibiting structural and functional characteristics of a native tissue.

2. The method of claim 1, wherein the native tissue is one that contains electrically excitable cells and is subject to electrical stimulation in vivo.

3. The method of claim 2, wherein the native tissue is selected from the group consisting of cardiac muscle tissue, striated skeletal muscle tissue, smooth muscle tissue, bone, vasculature, and nerve tissue.

4. The method of claim 1, wherein cultivating the cell-seeded construct comprises implanting the cell-seeded construct in vivo and placing the cell-seeded construct in electrical communication with a source of biomimetic electrical stimulation.

5. The method of claim 1, wherein the substrate is biocompatible.

6. The method of claim 1, wherein the substrate is biodegradable.

7. The method of claim 1, wherein the substrate is non-biodegradable.

8. The method of claim 1, wherein the substrate has a dry thickness of at least 1.5 mm.

9. The method of claim 1, wherein the substrate comprises a polymer selected from the group consisting of a naturally-occurring polymer, a synthetic polymer, and any combination thereof.

10. The method of claim 1, wherein the mammalian cells comprise cells of one cell type.

11. The method of claim 1, wherein the mammalian cells comprise cells of at least two different cell types.

12. The method of claim 1, wherein the mammalian cells are neonatal cells.

13. The method of claim 1, wherein the mammalian cells are adult or aged cells.

14. The method of claim 1, wherein the mammalian cells are progenitor cells.

15. The method of claim 14, wherein the progenitor cells are derived from a tissue selected from the group consisting of bone marrow, fat and umbilical cord.

16. The method of claim 1, wherein the mammalian cells are adult stem cells.

17. The method of claim 1, wherein the mammalian cells are embryonic stem cells.

18. The method of claim 1, wherein the mammalian cells are mesenchymal stem cells (MSC).

19. The method of claim 1, wherein the mammalian cells are genetically transformed cells.

20. The method of claim 1, wherein the mammalian cells are human cells.

21. The method of claim 1, further comprising: harvesting mammalian cells from an individual; and cultivating the harvested cells in vitro before contacting the substrate.

22. The method of claim 21, wherein the individual is intended to be the recipient of the construct.

23. The method of claim 1, wherein the mammalian cells are cells from an established cell line.

24. The method of claim 1, wherein the construct is a cardiac muscle construct, and wherein the mammalian cells are selected from the group consisting of cardiomyocytes, endocardial cells, cardiac adrenergic cells, cardiac fibroblasts, vascular endothelial cells, smooth muscle cells, cardiac progenitor cells, adult stem cells, embryonic stem cells, mesenchymal stem cells and any combination thereof.

25. The method of claim 24, wherein the mammalian cells are selected from the group consisting of cardiomyocytes, endocardial cells, cardiac adrenergic cells, cardiac fibroblasts, vascular endothelial cells, smooth muscle cells, cardiac progenitor cells, and any combination thereof.

26. The method of claim 1, wherein cultivating the cell-seeded construct comprises employing conditions selected to promote cellular production of extracellular matrix components.

27. The method of claim 1, wherein cultivating the cell-seeded construct comprises employing conditions selected to promote cell proliferation.

28. The method of claim 1, wherein cultivating the cell-seeded construct comprises employing conditions selected to promote cell differentiation.

29. The method of claim 1, wherein cultivating the cell-seeded construct comprises employing conditions selected to allow the formation of a three-dimensional construct with a predetermined thickness.

30. The method of claim 1, wherein cultivating the cell-seeded construct comprises employing conditions selected to allow the formation of a three-dimensional construct, wherein the mammalian cells are organized on the substrate with a defined orientation.

31. The method of claim 1, wherein the electrical stimulation mimics the electrical stimulation received by a cardiac muscle tissue in vivo.

32. The method of claim 31, wherein the electrical stimulation promotes differentiation of progenitor cells into cardiac myocytes.

33. The method of claim 31, wherein the electrical stimulation promotes differentiation of stem cells into cardiac myocytes.

34. The method of claim 1, wherein the electrical stimulation mimics the electrical stimulation received by a native tissue in vivo, the native tissue being selected from the group consisting of striated skeletal muscle tissue, smooth muscle tissue, bone, vasculature, and nerve tissue.

35. The method of claim 1, further comprising stimulating the cell-seeded construct chemically.

36. The method of claim 1, further comprising treating the three-dimensional tissue-engineered construct with at least one biologically active agent.

37. The method of claim 36, wherein the biologically active agent is selected from the group consisting of growth factors, adhesion factors, soluble extracellular matrix proteins, antibiotics, agents that enhance vascularization, agents that enhance cell differentiation, agents that enhance tissue differentiation, agents that inhibit fibrosis, agents that inhibit tumorigenesis, agents that enhance cell proliferation, agents that inhibit cell proliferation, agents that inhibit scaffold degradation, agents that enhance scaffold degradation, agents that improve histocompatibility, and agents that enhance hemocompatibility.

38. The method of claim 1, further comprising storing the three-dimensional tissue-engineered construct.

39. The method of claim 1 further comprising:
capturing a tissue response with the biomimetic electrical stimulation so as to achieve a stable tissue response.

40. The method of claim 1, wherein the substrate comprises a collagen sponge.

41. The method of claim 1, wherein the substrate comprises a water-insoluble, partial HCl salt of purified bovine dermal collagen formed as a sponge with interconnected pores.

42. The method of claim 1, wherein the substrate comprises a naturally-occurring polymer selected from the following group: starch, dextran, cellulose, and hyaluronic acid.

43. The method of claim 42, wherein the starch, dextran, or cellulose has been modified physically or chemically to affect one or more of its properties selected from the following group: characteristics in the hydrated state, solubility, half-life in vivo.

44. The method of claim 1, wherein the substrate comprises collagen or gelatin.

45. The method of claim 1, wherein the substrate comprises a polymer selected from the following group: polyanhydrides, polyorthoesters, polyphosphazenes, polycaprolactones, polyamides, polyurethanes, polyesteramides, polydioxanones, polyacetals, polyketals, polycarbonates, polyorthocarbonates, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or higher poly-monomer polymers thereof, or combinations or mixtures thereof.

* * * * *